(12) United States Patent
Feldmann

(10) Patent No.: US 9,963,665 B2
(45) Date of Patent: May 8, 2018

(54) BIOGAS PLANT AND PROCESS FOR THE PRODUCTION OF BIOGAS FROM LIGNEOUS RENEWABLE RESOURCES

(75) Inventor: Michael Feldmann, Marburg (DE)

(73) Assignee: Jan A. Meissner, Kusnacht (CH)

( * ) Notice: Subject to any disclaimer, the term of this patent is extended or adjusted under 35 U.S.C. 154(b) by 1239 days.

(21) Appl. No.: 12/666,635

(22) PCT Filed: Jul. 27, 2007

(86) PCT No.: PCT/EP2007/006681
§ 371 (c)(1),
(2), (4) Date: Jun. 21, 2010

(87) PCT Pub. No.: WO2009/000305
PCT Pub. Date: Dec. 31, 2008

(65) Prior Publication Data
US 2010/0285556 A1     Nov. 11, 2010

(30) Foreign Application Priority Data

Jun. 27, 2007  (DE) .................. 10 2007 029 700

(51) Int. Cl.
| C12M 1/16 | (2006.01) |
| C12M 1/107 | (2006.01) |
| C12M 3/00 | (2006.01) |
| C12M 1/00 | (2006.01) |

(52) U.S. Cl.
CPC ............ *C12M 21/16* (2013.01); *C12M 21/04* (2013.01); *C12M 23/44* (2013.01); *C12M 29/02* (2013.01); *Y02E 50/343* (2013.01)

(58) Field of Classification Search
USPC .................. 435/289.1, 300.1; 99/485
See application file for complete search history.

(56) References Cited

U.S. PATENT DOCUMENTS

| 3,302,246 A * | 2/1967 | Rionda ..................... 19/5 R |
| 4,187,775 A * | 2/1980 | Flender ..................... 100/39 |
| 4,997,488 A * | 3/1991 | Gould et al. ............... 127/37 |
| 5,147,502 A * | 9/1992 | Carlson et al. ............. 162/4 |
| 5,269,634 A | 12/1993 | Chynoweth |

(Continued)

FOREIGN PATENT DOCUMENTS

| DE | 33 41 691 A1 | 5/1985 |
| DE | 43 08 920 A1 | 9/1994 |

(Continued)

OTHER PUBLICATIONS

International Search Report for international application No. PCT/EP2007/006681 dated Jun. 4, 2008.

(Continued)

*Primary Examiner* — Nathan A Bowers
*Assistant Examiner* — Lydia Edwards
(74) *Attorney, Agent, or Firm* — Foley & Lardner LLP

(57) ABSTRACT

The present invention relates to a biogas plant and to a process for the production of biogas from ligneous renewable resources, in particular straw. Means are provided for pre-treating the ligneous renewable resource in order to bring about chemical, thermal and/or mechanical digestion of said resource before it is introduced into a fermenter in which anaerobic bacterial fermentation takes place.

58 Claims, 10 Drawing Sheets

(56) References Cited

U.S. PATENT DOCUMENTS

Figure 1:
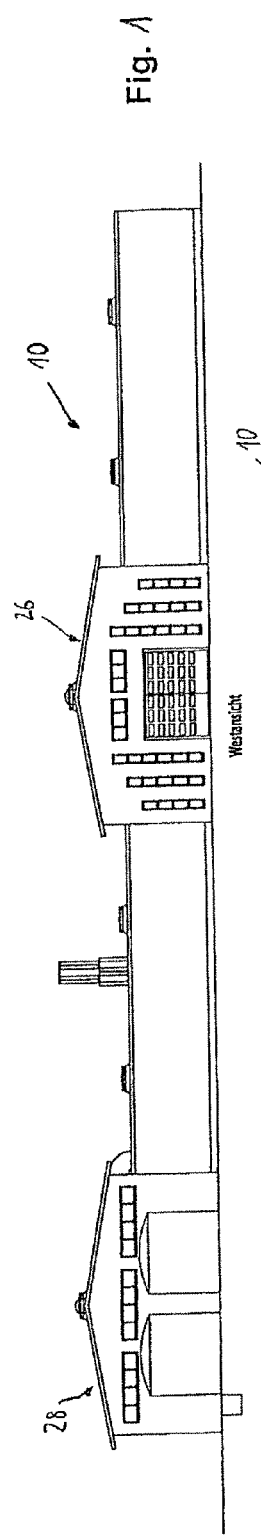

| | | | | |
|---|---|---|---|---|
| 6,299,774 | B1* | 10/2001 | Ainsworth | C02F 3/28 210/178 |
| 7,211,429 | B1* | 5/2007 | Rudas | 435/262 |
| 2002/0148575 | A1* | 10/2002 | Wingerson | D21C 1/02 162/14 |
| 2002/0192774 | A1* | 12/2002 | Ahring | C02F 9/00 435/162 |
| 2003/0176669 | A1* | 9/2003 | Thorre | 536/1.11 |
| 2006/0024801 | A1 | 2/2006 | Holtzapple et al. | |
| 2006/0275895 | A1* | 12/2006 | Jensen et al. | 435/300.1 |
| 2007/0193063 | A1* | 8/2007 | Lundell | F26B 1/00 34/543 |
| 2008/0085548 | A1* | 4/2008 | Lutz | 435/286.5 |

FOREIGN PATENT DOCUMENTS

| | | |
|---|---|---|
| DE | 195 32 359 A1 | 3/1997 |
| DE | 196 33 928 A1 | 2/1998 |
| DE | 198 57 870 A1 | 6/2000 |
| DE | 100 21 383 A1 | 11/2001 |
| DE | 100 50 623 A1 | 4/2002 |
| DE | 2020040 12 746 U1 | 12/2004 |
| DE | 2020060 03 293 U1 | 5/2006 |
| DE | 10 2005 019445 A1 | 10/2006 |
| EP | 0 056 202 A | 7/1982 |
| EP | 0 286 100 A | 10/1988 |
| EP | 0 934 998 A | 8/1999 |
| EP | 1 681 344 A | 7/2006 |
| GB | 2 073 166 A | 10/1981 |
| WO | WO-2009/000307 A1 | 12/2008 |
| WO | WO-2009/000309 A1 | 12/2008 |

OTHER PUBLICATIONS

International Search Report for international application No. PCT/EP2007/009809 dated Jul. 7, 2008.

International Search Report for international application No. PCT/EP2007/010892 dated Sep. 5, 2008.

Dictionary excerpt: Langenscheidts Fachwörterbuch Technik und angewandte Wissenschagten; Deutsch-Englisch; p. 146.

* cited by examiner

BIOGAS PLANT AND PROCESS FOR THE PRODUCTION OF BIOGAS FROM LIGNEOUS RENEWABLE RESOURCES

The present invention relates to a biogas plant and in particular to a biomass power plant for the production of biogas and to a process for the production of biogas from ligneous renewable resources, in particular from straw.

Straw represents an important example of a strongly lignified renewable resource, which is often referred to in the following disclosure. However, it is understood that everything explained with reference to straw applies in principle also to other ligneous renewable resources, without this always being pointed out in this document.

At present straw is practically never used in biogas plants as a fermentation substrate; in biogas plants straw is only present indirectly and in small quantities as a bedding or litter material contained in the solid manure. For reasons that will be explained below, there is a technical prejudice to the use of straw as a fermentation substrate.

At present in Germany there are more than 3,500 wet-fermentation plants in use, compared to only about 20 plants for solid-state fermentation (dry fermentation) of renewable resources. In wet-fermentation plants the use of straw is not considered for the very reason that the wet fermentation substance needs to be stirred with paddle wheels or propellers, and straw would get caught in the paddles or propellers. For this reasons it is rare that straw-containing solid manure is used in wet-fermentation plants; instead, liquid manure is predominantly used. If straw is shredded in order to overcome this mechanical problem, the shredded straw floats and therefore does not mix with the wet fermentation substrate. Furthermore, as a rule, straw blocks the drains or the overflows of wet-fermenters. For these reasons alone straw is presently not considered as a fermentation substrate in wet-fermentation plants.

Existing biomass power plants or biogas plants for the production of biogas according to the solid-state fermentation process are typically small agricultural plants comprising two to six fermenters. According to the recently published final report "Monitoring of the Impacts of Amending the Renewable Energy Sources Act on the Development of the Electricity Production from Biomass" ("Monitoring zur Wirkung des novellierten Erneuerbare-Energien-Gesetzes (EEG) auf die Entwicklung der Stromerzeugung aus Biomasse") which was prepared on behalf of the Federal Ministry for the Environment, Nature Conservation and Nuclear Safety ("Bundesministeriums für Umwelt, Naturschutz und Reaktorsicherheit") dry fermentation has not reached the stage of being ready for the market. The Federal Ministry tends to consider the plants that are in operation as demonstrator plants (see page 52, FIGS. 5-2 of the above-mentioned final report).

In principle it would be quite feasible to use straw as a fermentation substrate in such solid state fermentation plants. However, this is presently not happening because it is generally assumed that the gas yield from straw is insufficient.

Instead of using ligneous renewable resources, known solid-state fermentation processes conventionally predominantly use biodegradable waste as well as solid cow manure, pig manure and dry chicken manure. Furthermore, predominantly lightly lignified renewable resources such as, for example, freshly harvested grass, silage comprising grass, cut whole cereal plants and cut whole corn plants are used, as are hay, potatoes and shredded beet. Since presently-known biogas plants with solid-state fermentation are typically located in rural regions, for example on a farm, and only have a comparatively low throughput, the requirement for fermentation mass is normally covered by the farmer's own holdings and possibly those of neighbouring operations. However, for solid-state fermentation plants that are larger than has been the case so far, obtaining suitable fermentation substrates in adequate quantities and at economical conditions poses a problem.

It is an object of the present invention to provide a biogas plant, in particular a biomass power plant, and a method for the production of biogas, which plant and method solve the problem of procuring and processing adequate quantities of suitable fermentation substrates at economical conditions, in particular for larger plants that operate on an industrial scale.

This object is met by a biogas plant for and a process for the production of biogas, according to the embodiments described herein.

According to the invention, the biogas plant provides for a device for chemical, mechanical and/or thermal disintegration of ligneous renewable resources, in particular of straw. By means of the disintegration of lignified renewable resources, for example straw, contrary to prevailing opinions, it is possible to achieve considerable gas yield with these resources too. Consequently, biogas production, in particular biogas production according to the solid-state fermentation process, becomes accessible to a new class of renewable resources, in particular to straw, which is available in large quantities and at economical conditions. Straw can be used as a supplement to the conventional fresh material, for example silage comprising cut green plants, silage comprising entire cereal plants etc., thus ensuring the supply for even a large number of large and very large biomass power plants, for example each comprising 20 or more fermenters and an electrical output in excess of 5,000 kW at economical conditions.

For the disintegration of ligneous renewable resources the device preferably comprises a device for saturated-steam treatment. The device for saturated-steam treatment preferably comprises a pressure vessel and means that are suitable for generating steam in the pressure vessel at a pressure of between 20 and 30 bar, and at a temperature of between 180° C. and 250° C. Saturated-steam treatment takes place at the pressures and temperatures described, and typically lasts from 5 to 15 minutes. Below, the function of saturated-steam treatment is described with reference to the example of wheat straw.

The composition of wheat straw is approximately 40% cellulose, 23% arabinoxylane (hemicellulose) and 21% lignin, wherein all three principal components have a tightly-packed structure. Lignin, which cannot be disintegrated by micro-organisms and which blocks bacterial access to cellulose and to hemicellulose, is the significant obstacle to the biochemical utilisation of cellulose and hemicellulose. During saturated-steam treatment the lignin structures are softened or melted, but during the comparatively short treatment duration are essentially not dissolved out of the stalks. After saturated-steam treatment the lignin returns to its solidified state. However, during solidification of the lignin, disaggregated droplet-like lignin structures form that leave an adequate number of interstitial spaces through which first the aqueous organic acids and then the bacteria can gain access to the cellulose and the arabinoxylane, wherein said acids and bacteria decompose said cellulose and arabinoxylane in the known four-stage anaerobic fermentation.

In the presently described saturated-steam treatment, it is primarily the microscopic structure of the lignin that is altered, however, the lignin is not dissolved out of the stalks of straw. In particular, the structure of the stalks of straw as such is preserved in saturated-steam treatment. This represents a significant difference from thermal pressure hydrolysis, which is basically carried out under similar conditions but for longer periods of time, wherein in thermal pressure hydrolysis true hydrolysis takes place, in other words the dissolution of previously solid or dry materials in water. As a result of thermal pressure hydrolysis the structure of the stalks of straw is dissolved, with a syrup-like suspension forming.

In an advantageous improvement, the device for the disintegration of ligneous renewable resources comprises a container for soaking, for example in water, said renewable resources prior to saturated-steam treatment. When the soaked ligneous renewable resources are subjected to saturated-steam treatment, the water that has been soaked up flashes instantaneously into steam, and as a result of this the ligno-cellulose structures tear open, and the cellulose becomes still better accessible to bacteria.

An advantageous embodiment provides for a device for the mechanical size reduction of the ligneous renewable resources, by means of which size reduction the ligneous renewable resource can be mechanically disintegrated, for example by shredding, prior to saturated-steam treatment. This further contributes to the dissolution of the lignin structures and facilitates subsequent fermentation.

As an alternative to saturated-steam treatment, grinding in a hammer mill can take place. This form of disintegration mechanically destroys the lignin structures. However, when the solid-state fermentation process is applied, grinding alone makes little sense because a dough-like slurry would form that would agglutinate the fermentation mass thus preventing percolation.

However, as an alternative, the ligneous renewable resource can also be disintegrated in bale form, which significantly facilitates in particular its transport and handling, as will be explained in more detail below. Since the structure, for example of stalks of straw, is preserved during saturated-steam treatment, bales of straw too retain their shape during saturated-steam treatment, and after this treatment can be transported in a simple and efficient manner. Bales are furthermore associated with a particular advantage in that they can be placed at the very bottom of a garage-type fermenter, and consequently the fill height of the fermenter can be increased. Basically, the fill height of the fermenter is limited in that from a certain height of the substrate in the fermenter onwards, the pressure at the floor of said fermenter becomes so high that the substrate becomes too compressed to allow percolate to trickle through. However, layers of bales of straw that are placed at the very bottom of a fermenter are far more stable under pressure than is conventional fermentation substrate. Even at high pressure the layer of bales of straw is still permeable to percolate, so that the normal fill height in the fermenter can still be filled onto the layer of straw bales. Fermenters can therefore be designed so as to be higher than usual, namely by the height of the layer of bales of straw, which keeps the fermenter-specific technical costs (door, gas installations, sensor arrangement, flaps and openings, percolate nozzles, discharges, pipe system, pumps etc.) constant, thus improving the efficiency of the biogas plant as a whole.

In order to improve the efficiency of a soaking phase and/or a saturated-steam treatment of bales comprising a ligneous renewable resource, in particular of bales of straw, an advantageous improvement provides means for perforating the bales. In this arrangement the means for perforating are preferably suitable for perforating a bale from two sides in such a manner that the holes resulting from perforation from one side, and the holes resulting from perforation from the other side are separated by bridges of material. As a result of such perforation of the bale, both the soaking of the bale and the subsequent saturated-steam treatment become more efficient.

In an advantageous improvement, the device for saturated-steam treatment comprises at least one lance onto which a bale containing a ligneous renewable resource can be speared, wherein the lance comprises an interior hollow space into which steam can be introduced, and comprises a multitude of openings through which the steam can issue from the hollow space. As a result of this the hot steam that is used in the saturated-steam treatment and that is highly pressurised can be introduced through the lance into the bale, and consequently the saturated steam atmosphere also reaches to an outstanding extent the material in the interior of the bale. In a simpler version, in which the saturated-steam atmosphere would be introduced in an obvious manner into the pressure vessel, a problem may arise in that it is likely that the air present in the bale would become compressed in an inner section of the bale, but would not mix sufficiently quickly with the steam, so that the saturated-steam treatment in this inner section of the bale would be less effective.

If a loose ligneous renewable resource is used, in the pressure vessel preferably a container that is permeable to steam is provided for retaining said ligneous renewable resource. Furthermore, preferably means for transporting into the pressure container and out of the pressure container the container that is permeable to steam are provided, for example rails or a roller path.

In a particularly advantageous improvement the pressure vessel comprises a top opening, through which a loose ligneous renewable resource can be loaded into said pressure vessel, and a bottom opening through which the loose ligneous renewable resource can fall out of the container that is permeable to steam. As will be explained in more detail below with reference to an exemplary embodiment, with such a design it is possible to carry out quasi-continuous saturated-steam treatment during which the loose ligneous renewable resource is poured batch-by-batch into the container; the pressure vessel is then closed for saturated-steam treatment to take place; the treated loose material is then made to drop from the container through the bottom opening; and finally a subsequent batch is dropped into the container through the top opening.

In an advantageous improvement, for saturated-steam treatment the device can comprise pressure vessels that are interconnected by means of pipelines. In this manner a multitude of pressure vessels can be supplied by a single steam source, for example a single steam reservoir, which significantly improves the efficiency, in particular in the case of larger power plants.

In an advantageous improvement, for the disintegration of a ligneous renewable resource, the device comprises a container for soaking said ligneous renewable resource in a water-lye solution, a water-acid solution, percolate or liquid manure. Such soaking is one example of the chemical disintegration mentioned in the introduction. Such soaking can, in particular, be carried out following saturated-steam treatment, namely both in the case of a loose renewable resource, and in the case of a bale-shaped renewable resource, wherein the bales in this case are preferably perforated in the manner described above. By means of this soaking (weakly aerobic) prehydrolysis is initiated, which takes place before placement in the fermenter. In addition, after soaking, and before placement in the fermenter, the soaked ligneous renewable resource can preferably be heated to 30 to 50° C. Such heating can be combined with conveying the ligneous renewable resource from the device for disintegration to the fermenter, as will be explained in more detail below. This prehydrolysis still further accelerates the subsequent anaerobic bacterial fermentation in the fermenter.

It should be noted that the design of the biogas plant and the process for the production of biogas operate well with the disintegration process described in the present document, without the addition of additional yeasts, fungi or enzymes. In fact the ligneous material is solely left to autohydrolysis and to bacterial hydrolysis. The use of bacteria instead of yeasts, fungi or enzymes is significantly more economical because the chemical and biochemical processes progress more quickly during bacterial hydrolysis than they do during enzymatic hydrolysis. Furthermore, when compared to the external use of enzymes and/or acids, considerable costs, which would otherwise be incurred for their procurement and handling, are saved.

An important improvement of the invention relates to the manner in which the additional process-related step of straw disintegration is integrated in the operation of the biogas plant. The device for the disintegration of the ligneous renewable resource is economically worthwhile in particular if the throughput of the plant, or of the biomass power plant, is high. However, presently-known biomass power plants for solid-state fermentation are usually very small and limited to rural regions. They comprise two to six smaller fermenters and achieve an effective electrical output of only 100 to 700 kW. This is due on the one hand to the fact that generally-speaking dry fermentation is not considered to be ready for the market, and on the other hand also due to the graduated minimum compensation of the EEG for electrical current supplied from renewable-resources plants, which compensation drops by up to 15% when a limit of 500 kW is exceeded. Furthermore, there is another factor mitigating against larger designs of biogas plants with dry fermentation in that according to the requirements of the financiers the required supply of fermentation substrate needs to be secured for many years in advance, and in that the operators, typically farmers, wish to rely on the renewable resources that can be produced by said operators themselves.

However, by means of the biogas plant according to the invention and the process according to the invention, which both also allow the use of strongly lignified renewable resources, the supply with fermentation substrate can also be ensured for far larger plants, because, for example, in cereal growing straw arises in far greater quantities than are presently required, and because, with corresponding (large-scale) technical application, straw can be transported comparatively economically even over larger distances. On the other hand, the investment costs and operating costs associated with a device for the disintegration of ligneous renewable resources are the more worthwhile the greater the throughput of the biogas plant. A correlation between the possibility for the disintegration of the ligneous renewable resources and the size of the biogas plant exists insofar as the device for the disintegration of the ligneous renewable resources makes a significant contribution to ensuring the supply of fermentation substrate even to larger biogas plants, and in that on the other hand the size of the biogas plant and the use of the economical substrate type of the ligneous renewable resource is the very key to rendering economical the investment for the disintegration in particular, and for the large biomass power plant as a whole.

In a hitherto unknown size of biogas plants, for example comprising 15 to 30 large garage-type fermenters, the operation of the biogas plant, and in particular the transport of the fermentation substrate and of the fermentation residues, needs to be designed so as to be efficient. A further task consists of integrating the above-described disintegration of the ligneous renewable resource in the operational process of the biogas plant.

In an advantageous improvement the device for the chemical, mechanical and/or thermal disintegration of ligneous renewable resources is accommodated in a delivery and loading area of the biogas plant. The delivery and loading area preferably comprises stationary materials handling technology that is suitable for conveying fresh material from the delivery and loading area to a fermenter courtyard from which a multitude of fermenters of the garage-type are accessible. While in conventional biogas plants the fresh material and the fermentation residues are transported by means of a wheel loader, according to the present improvement stationary materials handling technology is provided by means of which even large quantities of fresh material can be conveyed efficiently to the fermenter courtyard and from there can be fed into the fermenters. Furthermore, such stationary materials handling technology makes it possible to enclose the entire biogas plant, as a result of which it is possible to prevent unpleasant odours from escaping into the environment, and it becomes possible to operate the biogas plant also in proximity to residential areas.

When the biogas plant is completely enclosed, in a manner of speaking the delivery and loading area provide an interface between the enclosed interior region of the plant and the exterior region, with said delivery and loading area thus being arranged in an outer section of the plant. In contrast to this, for logistics reasons the fermenter courtyard is arranged centrally in the plant. As a result of the stationary materials handling technology, the fresh material or the fermentation substrate can be conveyed from the delivery and loading area to the fermenter courtyard without this requiring transport vehicles that would emit exhaust gas within the enclosed region, and that would furthermore increase operating costs. Preferably there is slight negative pressure in the delivery and loading area so that even when fresh material is delivered and when fermentation residues are loaded only a small quantity of air reaches the outside, and thus unpleasant odours are kept to a minimum.

Preferably, the delivery and loading area comprises at least one enclosed delivery bunker for fresh material. Furthermore, preferably first conveyor means are provided that are suitable for conveying fresh material from the at least one delivery bunker for fresh material to a fresh-material bunker. These first conveyor means can, for example, comprise screw-type conveyors, elevators and conveyor belts on which the fresh material is conveyed from various delivery bunkers to the fresh-material hunker. This is associated with an advantage in that the fresh material is mixed for no other reason than it has been placed on the same heap from different delivery bunkers, so that subsequent mixing of the fresh material is no longer necessary, or no longer has to be undertaken as intensively. This fresh material described is not the ligneous renewable resource that would have to be disintegrated, but additional fresh material as used in hitherto-known biogas plants with solid-state fermentation.

Furthermore, the delivery and loading area preferably comprises second conveyor means, in particular a pusher blade, which means are suitable for conveying the fresh material through the fresh-material bunker in the direction of the fermenter courtyard. In this process the fresh-material bunker assumes a dual function: firstly it is used as a transport path from the delivery area to the fermenter courtyard, and secondly it is used as an interim storage area for fresh material. In this context it is important that the fresh material that is first placed in the fresh-material bunker also leaves said bunker first. This means that the fresh material that is supplied to the fermenter courtyard is always about the same age and is thus prehydrolised to the same extent. This results in a consistent substrate quality that is advantageous in the subsequent fermentation process.

Furthermore, in an advantageous improvement the delivery and loading area comprises an unloading point for ligneous renewable resources, in particular for straw, and in particular for baled straw. At the unloading point preferably a crane is provided that is suitable for picking up and transporting baled material.

Moreover, as mentioned above, the delivery and loading area comprises a device for the chemical, mechanical, and/or thermal disintegration of ligneous renewable resources, in particular of straw, which device is of the type described in the introduction. In particular, the device for disintegration can be designed, as described above, in a manner that the bale shape is preserved, so that the ligneous renewable resource, which has been pre-treated by disintegration, can be transported in the form of bales from the delivery and loading area to the fermenter courtyard, which renders transport and placement in the fermenter a very efficient process.

In this arrangement, preferably third conveyor means are provided, in particular roller conveyors or push-type conveyors, that are suitable for conveying individual bales or packets of bales along a bale channel to the fermenter courtyard.

Thus in the present advantageous improvement a distinction is made between loose fresh material and baled material. The baled material too is conveyed, by the third conveyor means and the bale channel, in a very efficient manner from the periphery to the fermenter courtyard, which makes it possible to achieve a high throughput with very low operating costs. Preferably, a transfer device is arranged on that end of the bale channel that faces the fermenter courtyard, which transfer device is suitable for removing packets of bales from the bale channel and passing them over as a packet to a wheel loader or forklift truck. As is explained in more detail below with reference to an exemplary embodiment, it is advantageous to place a layer of baled material on the bottom of each fermenter. According to this improvement of the invention this can in turn be effected particularly efficiently and quickly if suitable packets of bales, for example packets comprising eight bales, are passed over to the wheel loader or forklift truck, which packets can then be unloaded in the fermenter just the way they are.

Preferably, the delivery bunker, the fresh-material bunker and/or the bale channel are/is heatable, advantageously by means of waste heat that is generated by one or several gas engines. Preheating the fresh material compensates for temperature losses that arise during freshening of the fermentation mass in the salvage. This accelerates recommencement of biogas formation after freshening of the fermentation mass. Furthermore, this makes possible the above-described weakly aerobic prehydrolysis which shortens the time required for complete fermentation of the fermentation mass and improves plant output (substrate throughput) and thus the plant's operating efficiency.

An advantageous improvement provides for a fermentation residues bunker that for the placement of fermentation residues is accessible from the fermenter courtyard. The fermentation residues bunker preferably comprises stationary conveyor means that are suitable for transporting fermentation residues away through the fermentation residues bunker. In an advantageous improvement these stationary conveyor means are formed by screw-type conveyors that are arranged on the ends of the fermentation residues bunker. The fermentation residues bunker is preferably dimensioned so that it holds the expected quantity of fermentation residues that arises over at least two days.

The fermentation residues bunker according to the above-mentioned improvement of the invention has a triple function. Firstly it is used as an interim storage area for fermentation residues, and secondly it provides the transport device for fermentation residues from the central fermenter courtyard to the periphery. An adequate size of the fermentation residues bunker ensures that the fermentation residues can be kept in interim storage for at least two days so that they do not have to be collected on weekends, when truck traffic is restricted. Finally, as the third function, post fermentation takes place in the fermentation residues bunker, and for this reason said bunker is connected to the biogas system. In this way further biogas is obtained from the fermentation residues, which biogas would be lost in a more basic design.

At the inlet end of the fermentation residues bunker, preferably a feed bin for fermentation residues is arranged. The fermentation residues can thus be poured directly from the fermenter courtyard into the feed bin; thereafter they are automatically transported to the periphery.

Preferably, at the outlet end of the fermentation residues bunker a device for dehydrating the fermentation residues is provided. The fermentation residues comprise percolate that is rich in nutrients and bacteria, which percolate can be fed, by way of a circular pipeline, into the percolate circulation tanks described later, if there is a requirement for this. If such percolate is required, it is pressed, at the device for dehydration, from the fermentation residues, and by way of the circular pipeline it is fed to the percolate circulation tanks. Otherwise it is also possible to bypass the dehydration device; in this case the fermentation residues, which are in a wetter state, are transported away as they are.

In addition or as an alternative, a drying plant for the drying of fermentation residues can be provided, which drying plant preferably uses exhaust heat from a gas Otto engine for drying the fermentation residues. Furthermore, preferably a gasification plant is provided that is suitable for generating wood gas or weak gas from dried fermentation residues, according to the method of wood gasification, in particular based on carbonisation or pyrolysis. This weak gas can then be added to the biogas that has been produced by fermentation. As a result of this downstream gasification of the fermentation residues approximately another 20% of the biogas that arises can be produced as a wood gas/weak gas, and consequently the efficiency of the raw material for the production of gas is significantly improved. In particular there is a technical link between the use of ligneous renewable resources with preliminary disintegration on the one hand and the downstream wood gasification on the other hand. Gasification of the fermentation residues makes it possible to increase gas yield if, as a result of incomplete disintegration of the ligneous renewable resource, said yield turns out to be lower than would be biologically possible. Moreover, as the name itself indicates, ligneous materials are particularly suitable for wood gasification. To this extent the use of ligneous renewable resources as a fermentation substrate and the downstream wood gasification of fermentation residues complement each other in an ideal way.

While the above improvements of the invention relate to plants for solid-state fermentation, the invention is not limited to this. For example it is possible, as presented above, to mechanically disintegrate ligneous renewable resources by grinding or milling them, and as a result of this the lignin structures would also be torn open. For example, investigations undertaken by the inventor have shown that, contrary to widely held expert opinion, if ground straw were to be introduced into a wet-fermentation plant, this would result in considerable additional gas yield. This is because during grinding the sheet-like lignin structures are also destroyed. Both cellulose and arabinoxylane can then be dissolved in the aqueous organic acids that are contained in the fermentation mass, which organic acids are also contained in the liquid manure that is typically present in wet-fermentation plants and that are present to a still greater extent in pure renewable-resources wet-plants that operate without liquid manure. Consequently, biomass that up to now has been considered to be unsuitable becomes accessible to anaerobic methane-producing bacteria.

A similarly simple process for chemical disintegration is also possible in biogas plants for solid-state fermentation, either with or without grinding the ligneous renewable resource. In this arrangement, already some days before placement in the fermenter, the ligneous material is mixed with other fresh material, preferably with solid manure. Urea present in the solid manure can then in turn solubilise the lignin and render the cellulose and the arabinoxylane accessible to hydrolysis. The important point in this is that additionally or separately provided ligneous renewable resources are chemically disintegrated by the urea contained in the solid manure. In this process, mixing the loose ligneous material with the solid manure would typically take place some considerable time before placement in the fermenter, preferably a few days before placement. In a very simple embodiment of the invention, layers of solid manure and layers of ligneous material could be built up in the fermenter, at practically the same time, so as to alternate, wherein if applicable it is also possible for layers comprising other renewable resources that are not strongly lignified to be placed in-between. In this way the urea of the solid manure layer at the top can enter, with the percolate, the layer with the ligneous material and can at least partly dissolve the sheet-like lignin structures. It is also possible to mix loose ligneous material with the fermentation residues and if applicable with further renewable resources. In this process the acidic percolate ensures that the sheet-like lignin structures dissolve at least in part and that the material produces biogas, even if the yield is less than that achievable with the other above-described processes for disintegration, in particular with saturated-steam treatment.

Preferably, the inoculation material, which together with the fresh material re-enters the fermenter, is thoroughly fulled and squeezed before being mixed with the use of a mechanical press, for example a screw-type press, and as a result of this the material is at least to some extent mechanically disintegrated, and, furthermore, any nutrients still locked in are made available to anaerobic bacterial fermentation. In this arrangement the screw-type press can be of a mobile design, for example it can be arranged on a low-bed loader so that it can be driven on the fermenter courtyard to the respective fermenter.

An advantageous improvement furthermore provides a device for thermal pressure hydrolysis, either before or after having passed through the solid-state fermentation plant but prior to the disposal of the fermentation residues. Thermal pressure hydrolysis takes place under conditions that are similar to those described in the introduction in the context of the saturated-steam treatment, except the duration is longer, for example from 60 to 120 minutes.

During thermal pressure hydrolysis the lignin is completely dissolved out so that a syrupy suspension forms. Furthermore, true hydrolysis, in other words decomposition of polymers to monomers, takes place as a result of the physical effect of water and heat. The syrupy suspension can then be fed (back) to the fermentation process or it can be sold to enterprises which produce second-generation fuels from this material. In this process the lignin content and any further non-utilised organic substances are utilised. This is not possible with anaerobic bacterial fermentation.

Figure 2:
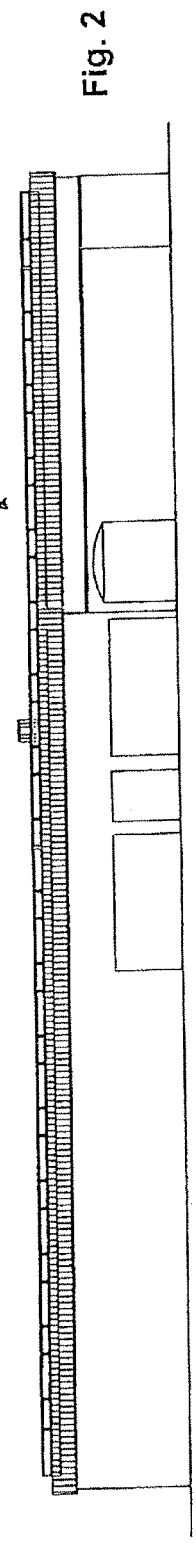
Figure 3:
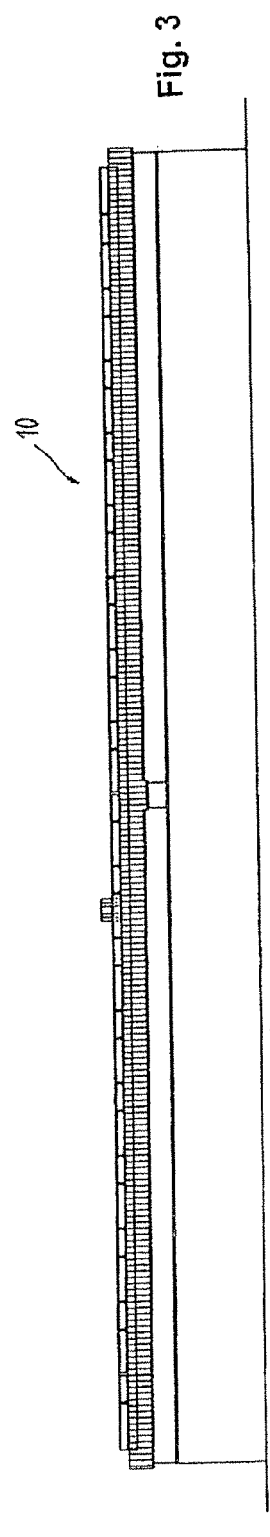
Figure 4:
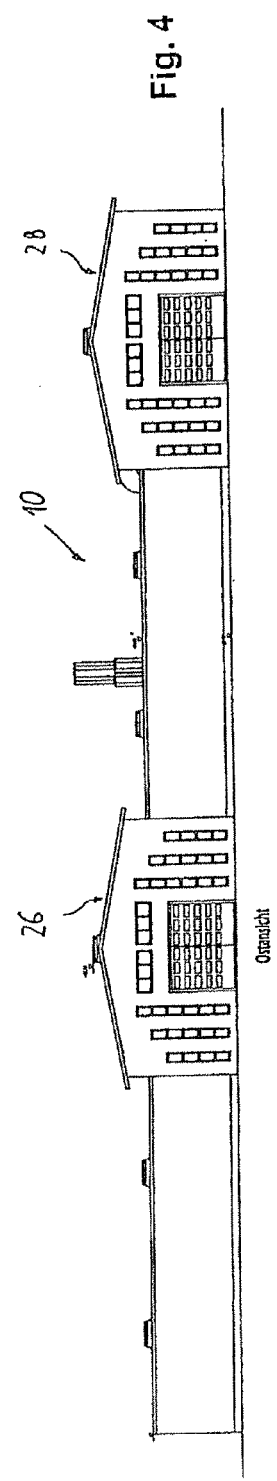
Figure 5:
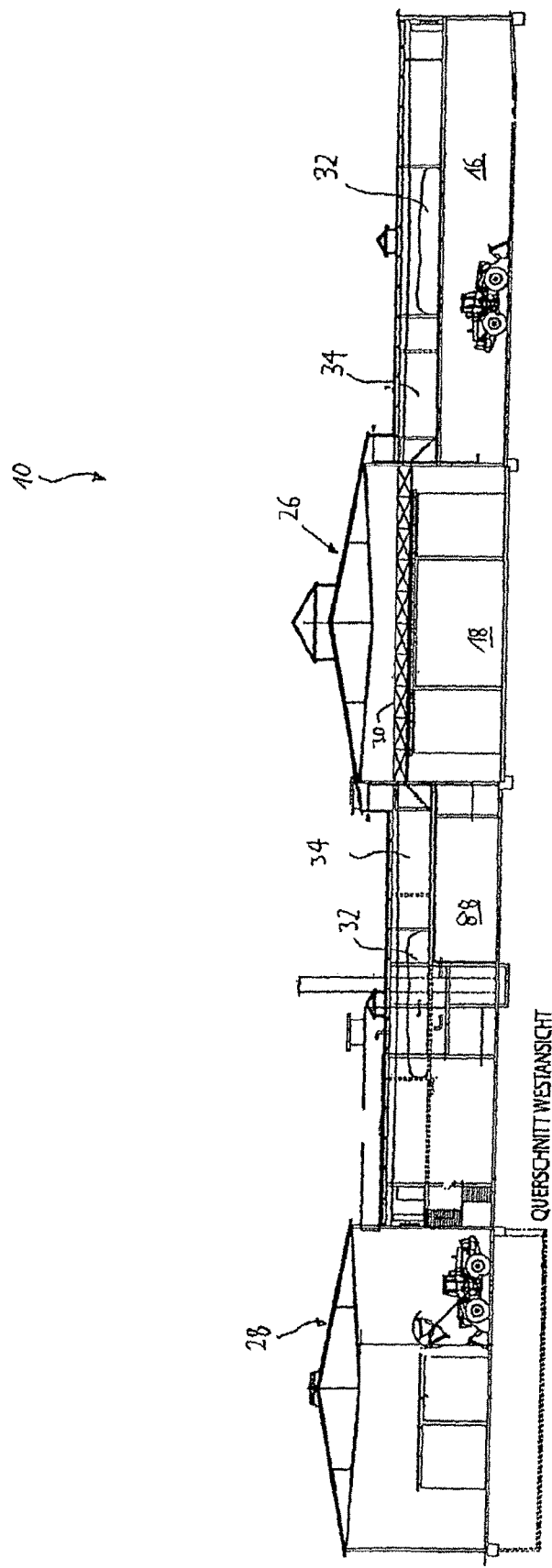
Figure 6:
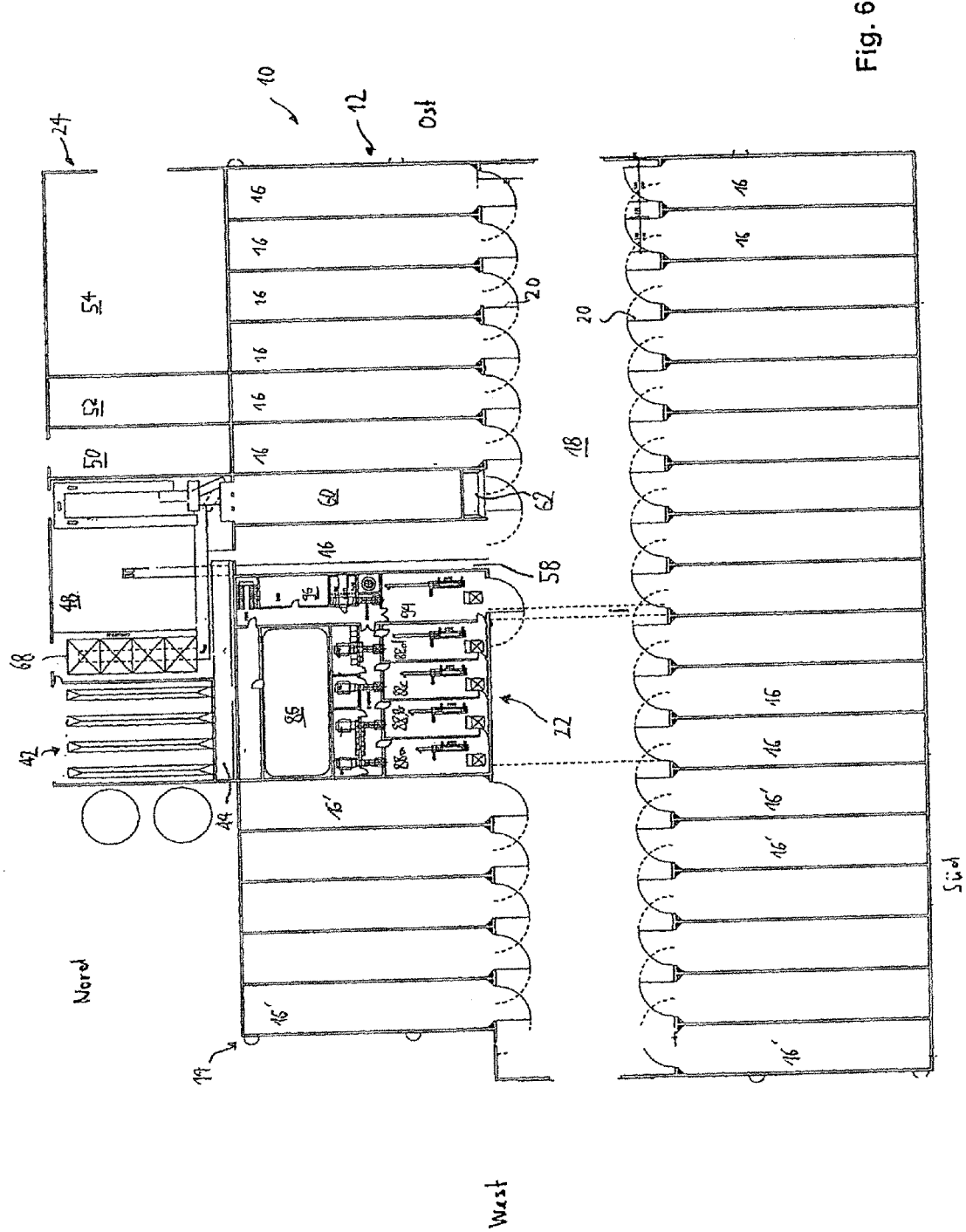
Figure 7:
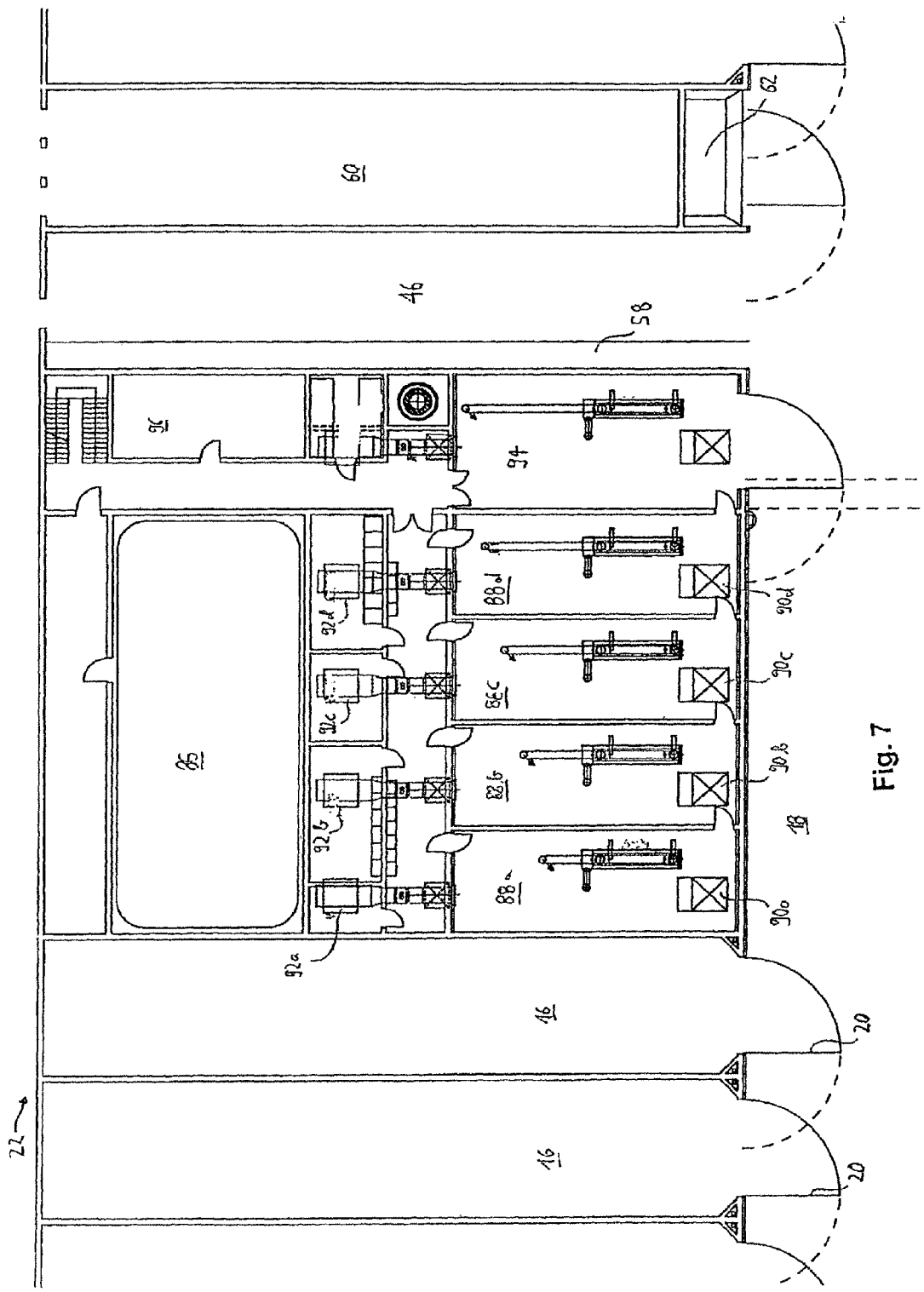
Figure 8:
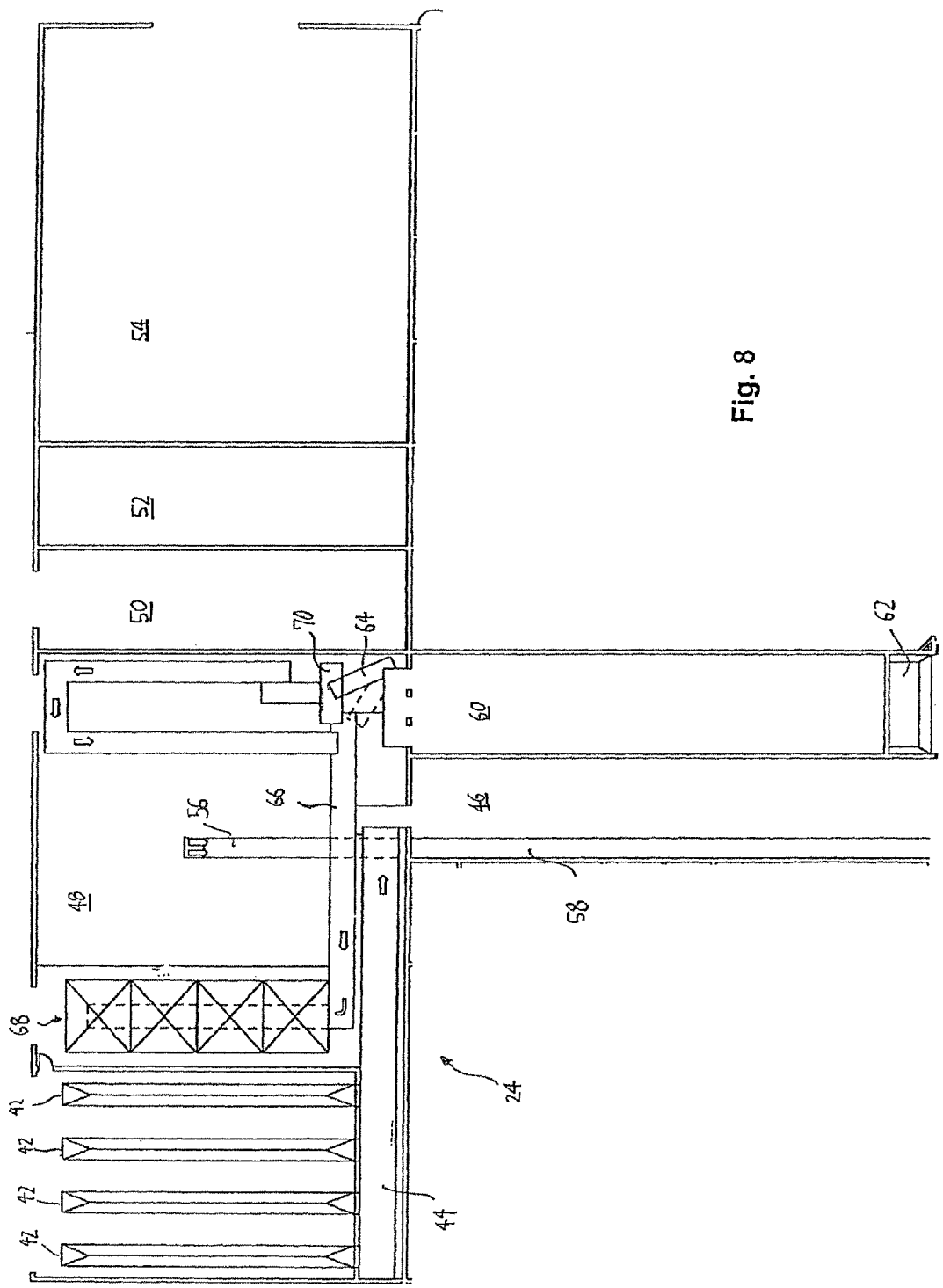
Figure 9:
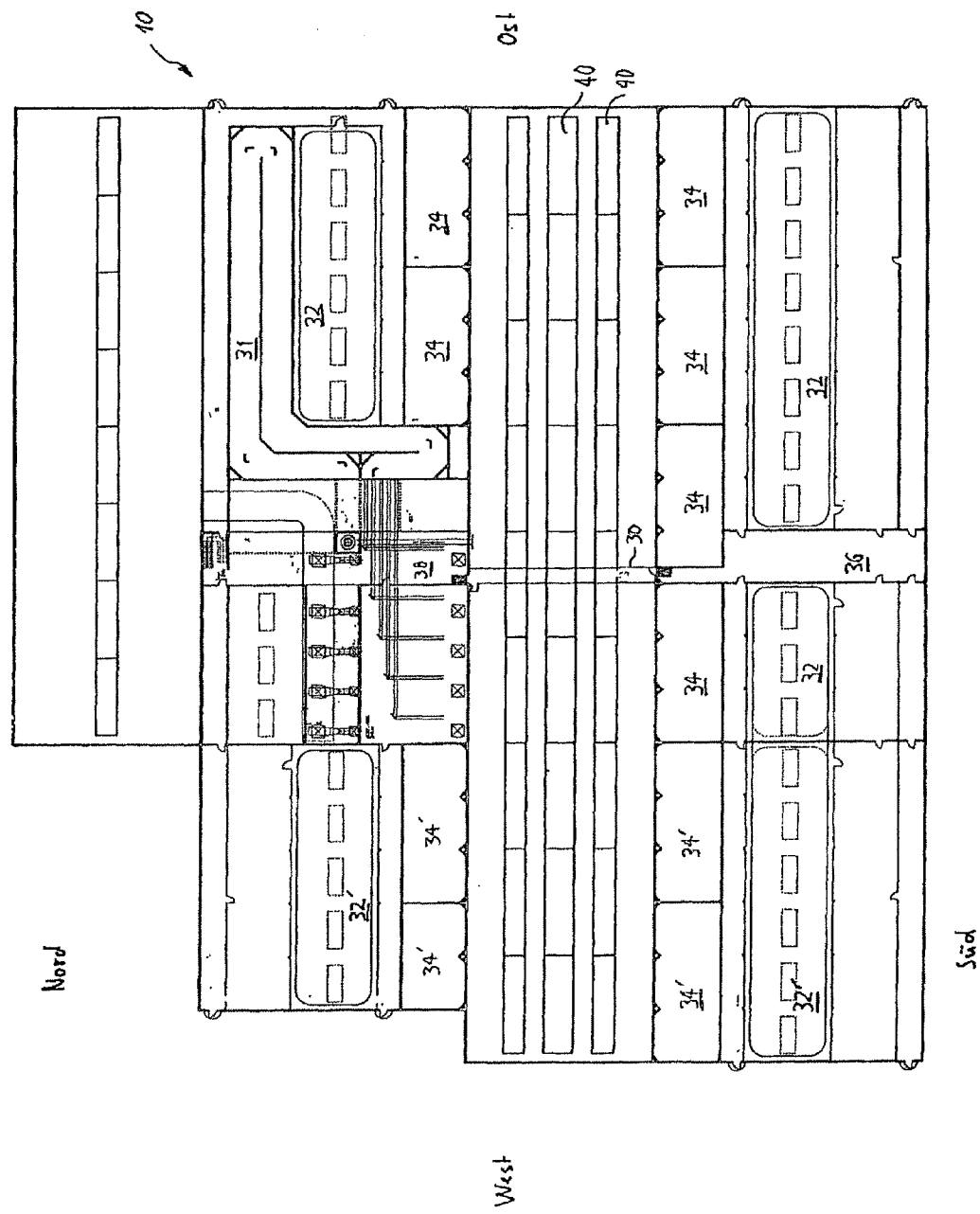
Figure 10:
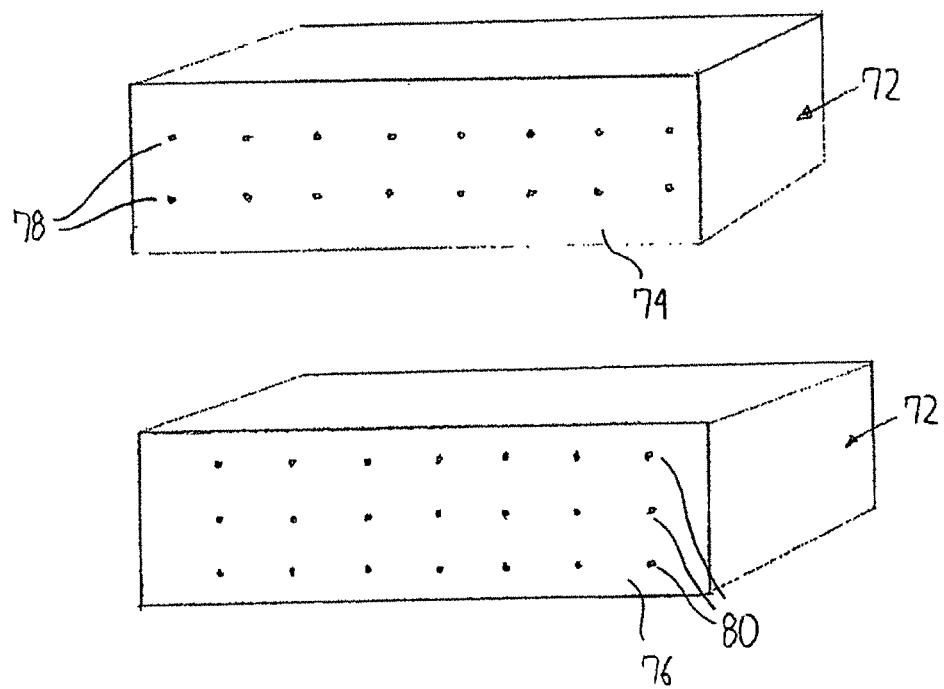
Figure 11:
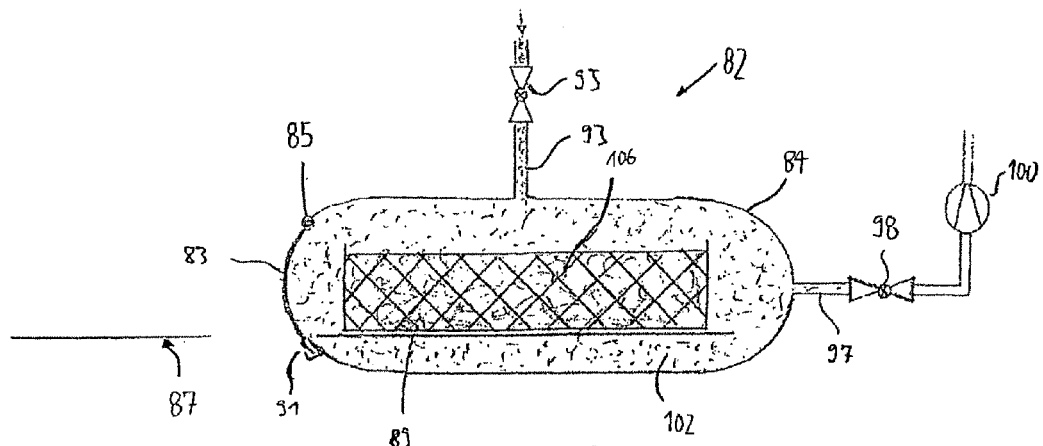
Figure 12:
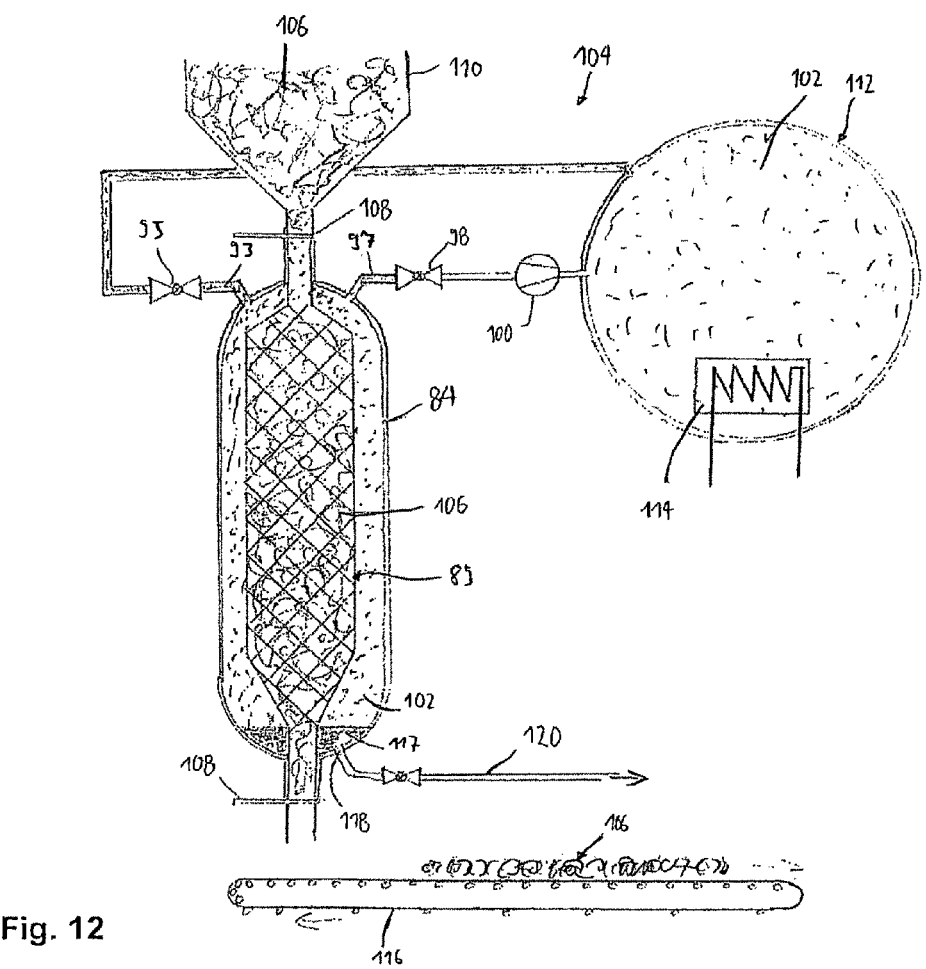
Figure 13:
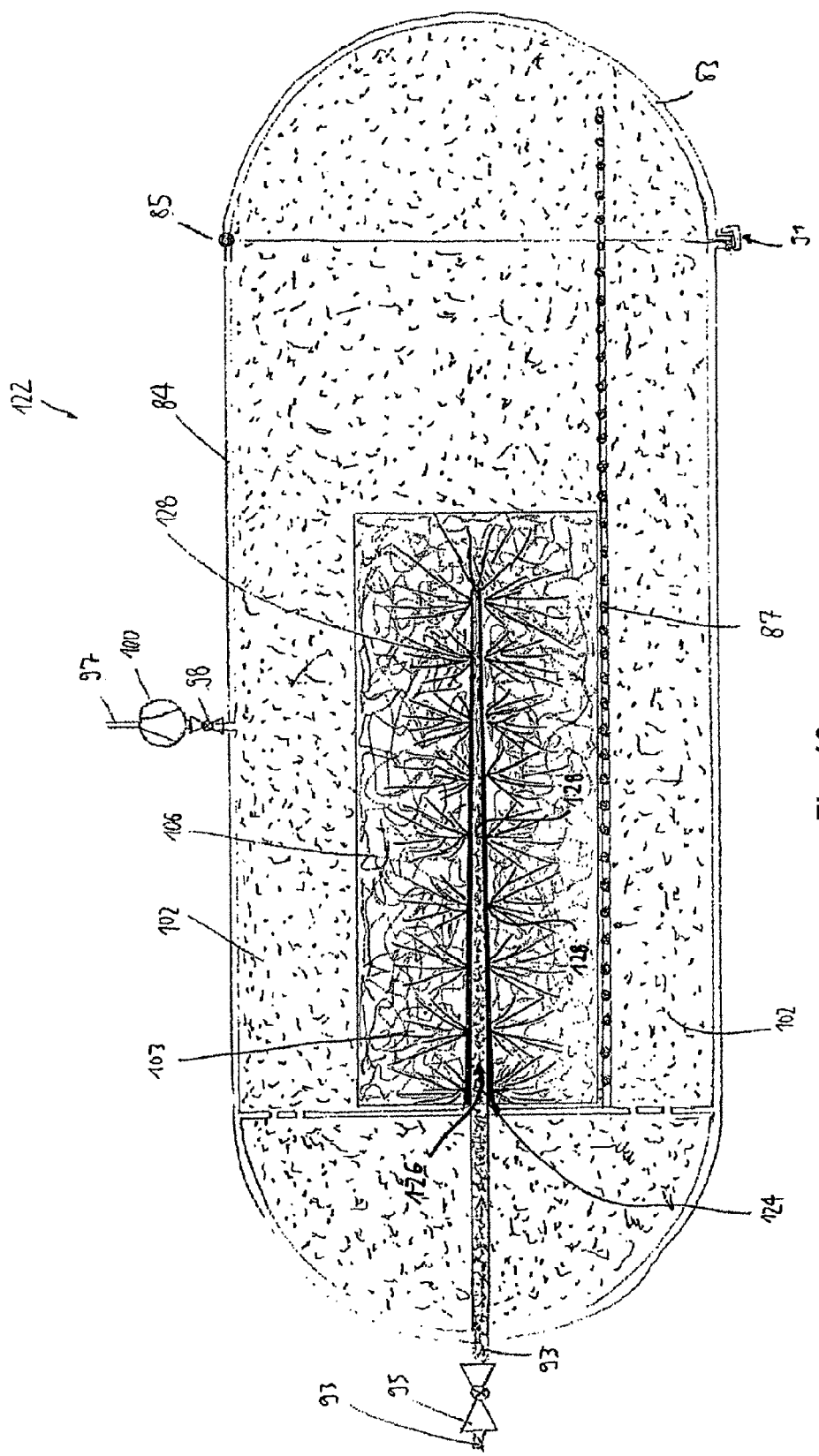
Figure 14:
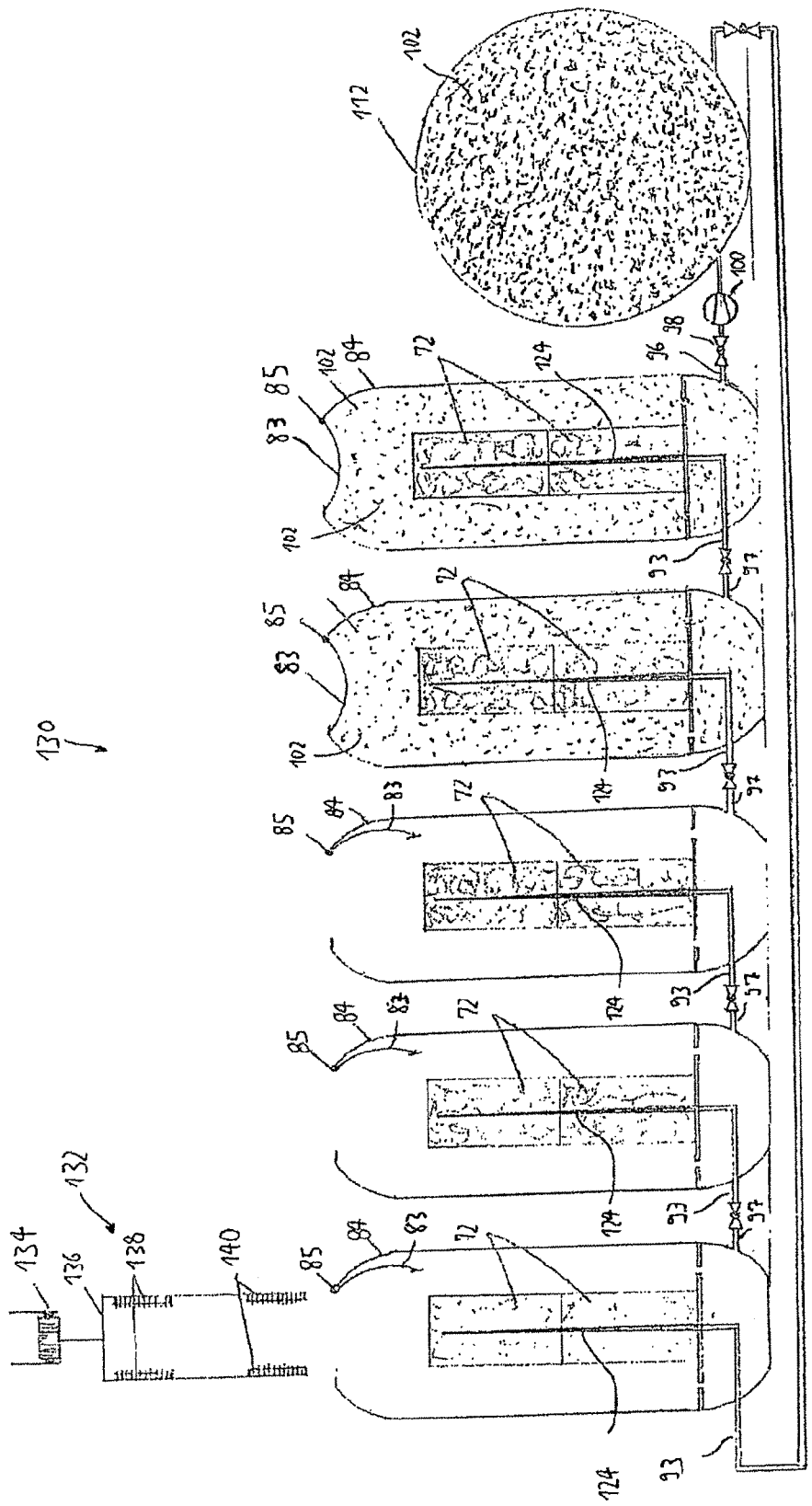

To provide a better understanding of the present invention, in the text below reference is made to the preferred exemplary embodiment shown in the drawings, which is described with the use of specific terminology. However, it should be pointed out that the scope of protection of the invention is not to be limited by this, because such changes and further modifications to the shown biogas plant and to the process shown, as well as further applications of the invention as disclosed therein, are regarded as the usual present or future knowledge of the average person skilled in the art. The figures show exemplary embodiments of the invention, as follows:

FIG. 1 a west elevation of a biomass power plant according to an improvement of the invention, FIG. 2 a north elevation of the biomass power plant of FIG. 1, FIG. 3 a south elevation of the biomass power plant of FIG. 1, FIG. 4 an east elevation of the biomass power plant of FIG. 1, FIG. 5 a cross-sectional view of the biomass power plant of FIG. 1, as viewed from the west, FIG. 6 a horizontal projection of the ground floor of the biomass power plant of FIG. 1, FIG. 7 an enlarged section of the horizontal projection of FIG. 6, showing a power and heat generating plant, FIG. 8 an enlarged section of the horizontal projection of FIG. 6, showing a delivery and loading area, FIG. 9 a horizontal projection of the upper floor of the biomass power plant of FIG. 1, FIG. 10 a diagrammatic illustration of two views of a perforated bale of straw, FIG. 11 a diagrammatic cross-sectional view of a device for saturated-steam treatment, FIG. 12 a diagrammatic cross-sectional view of a further device for saturated-steam treatment, designed for loose ligneous material, FIG. 13 a diagrammatic cross-sectional view of a device for saturated-steam treatment, designed for saturated-steam treatment of baled material, FIG. 14 a diagrammatic cross-sectional view of a device for saturated-steam treatment, comprising a multitude of pressure vessels.

Below, a biomass power plant 10 is described in detail as an exemplary embodiment of a biogas plant according to an embodiment of the invention. FIGS. 1 to 4 show four external views of the biomass power plant 10, and FIG. 5 shows a cross section thereof. FIG. 6 shows a horizontal projection of the ground floor of the biomass power plant 10. FIG. 7 shows an enlarged section of the horizontal projection of FIG. 10, in which a power and heat generating plant of the biomass power plant is shown. FIG. 8 shows another partial section of the horizontal projection of FIG. 6, in which a delivery and loading area is shown in an enlarged view. FIG. 9 shows a horizontal projection of the upper floor of the biomass power plant 10.

With reference to the horizontal projection of FIG. 6, the biomass power plant 10 comprises a base section 12 and an expansion section 14. The base section 12 comprises eighteen fermenters of the garage type, which fermenters are arranged in two rows, in the illustration of FIG. 5 in a northern and a southern row. Between the two rows of fermenters 16 there is a fermenter courtyard 18, onto which the doors 20 of the fermenters 16 open. It should be pointed out that for the sake of clarity not all the fermenters 16 and fermenter doors 20 in the figures comprise reference numbers.

Furthermore, the base section 12 comprises a power and heat generating plant 22, which in FIG. 7 is shown in an enlarged view and which will be described in detail below. Furthermore, the base section 12 comprises a delivery and loading area 24, which in FIG. 8 is shown in an enlarged view and which will also be described in more detail below.

As shown in FIGS. 1 to 6, the entire base section 12 is enclosed by a hall structure, of which in particular a hall section 26 of the fermenter courtyard and a hall section 28 of the delivery and loading area form part, as is particularly clearly shown in FIGS. 1,4 and 5. The entire hall construction or enclosure of the base section 12 is ventilated by a large central air exhaust device so that in the interior of the hall construction there is always slight negative pressure when compared to atmospheric pressure.

The expansion section 14 essentially comprises eleven additional fermenters 16' and an extension of the hall section 26 of the fermenter courtyard. If required, the expansion section 14 can provide up to eleven additional fermenters 16'. This means that the biomass power plant 10 is intended initially to be constructed and to take up operation without the expansion section 14. Operation will then show whether the existing eighteen fermenters 16 of the base section 12 produce sufficient biogas to supply the four gas engines (not shown) that are intended for the biomass power plant 10 with gas at full load. If this is not the case, the corresponding number of fermenters 16' in the expansion section 14 can be supplemented, wherein it is also possible that said expansion section 14 can be smaller than shown in FIG. 6. In other words, the biomass power plant 10 is of a modular design that is advantageous for achieving an optimal end configuration, because the exact biogas yield depends on a multitude of factors, among them the nature of the available fresh material, and can thus not be precisely predicted theoretically.

The northern and the southern fermenter rows are interconnected by a bridge 30, which bridge 30 is shown in particular in FIGS. 5, 6 and 9. The bridge 30 spans the fermenter courtyard 18 at a height that makes it possible for wheel loaders, of which two are shown in an exemplary manner in FIG. 5, to pass underneath it even with their loading buckets fully extended without touching or damaging the bridge.

With reference to FIG. 9 the upper floor of the biomass power plant 10 comprises three foil gas-storage devices 32 in the base section 12 and two further foil gas-storage devices 32' in the expansion section 14. The foil gas-storage devices 32 are clearly evident in the cross-sectional views of FIGS. 5 and 15. In the manner described in more detail below, said foil gas-storage devices 32 take up the biogas that is produced in the fermenters 16 or 16'.

Furthermore, the upper floor comprises five percolate circulation tanks 34 in the base section 12 and four percolate circulation tanks 34' in the expansion section 14, which tanks are also clearly shown in the cross-sectional views of FIG. 5. In each case a percolate circulation tank 34 is arranged above three fermenters 16, from which it receives percolate that is collected at the bottom of the fermenters and is pumped into the percolate circulation tank 34. The term "percolate" refers to the liquid component of the fermentation substance, which liquid component is in a sense similar to liquid manure.

Furthermore, the upper floor comprises a waste-gas cooling space 31, a southern room 36 comprising technical equipment and a northern room 38 comprising technical equipment, which are interconnected by way of the bridge 30. Furthermore, illumination strips 40 are arranged in the hall section 26 of the fermenter courtyard and in the hall section 28 of the delivery and loading area.

After this overview of the components of the biomass power plant 10, there follows a detailed description of the individual sections and components and their operating methods.

1. Fermenter Courtyard

The fermenter courtyard 18 is arranged in the centre of the biomass power plant 10. It is used as a transport path for fresh material supplied to the respective fermenters 16, 16' or for fermentation residue substance removed from the fermenters 16, 16'. Furthermore, the fermenter courtyard 18 is used as a mixing area on which the content of a fermenter is spread out, of which content approximately a fifth to a fourth is removed as fermentation residue, after which, in order to compensate for this removal and for the loss of mass resulting from gasification, approximately a third is supplemented by fresh material and is mixed with the old fermentation mass. This work can be carried out on the fermenter courtyard 18 by a large wheel loader as diagrammatically shown in FIG. 5. In the middle of the fermenter courtyard 18 there is a large drainage channel comprising a grid, into which drainage channel seepage liquid and released percolate flow. At the height of the bridge 30 the drainage channel comprises a collection well (not shown), from which the arising liquids are conveyed to one of the percolate circulation tanks 34 by way of a circular percolate pipeline (not shown).

2. Delivery and Loading Area

FIG. 8 shows an enlarged horizontal projection of the delivery and loading area 24. In the exemplary embodiment shown, as far as delivery is concerned, a distinction is made between loose fresh material and fresh structured material or fresh baled material. In the embodiment shown, four delivery bunkers 42 are provided for the loose fresh material, which delivery bunkers 42 are enclosed by the hall section 28 of the delivery and loading areas. A truck can reverse into the enclosed delivery bunker, and in that location can tip or remove by pusher the load of fresh material into the delivery bunkers 42. Since there is slight negative pressure in the entire delivery and loading area 24 hardly any unpleasant odours escape from the enclosure towards the outside. Each delivery bunker 42 comprises a floor that conically tapers off towards the bottom, wherein at the lowest point of said floor one or several dual screw-type conveyors (not shown) are provided that conveys/convey the fresh material horizontally to a bucket elevator (not shown), which conveys the fresh material to a conveyor belt 44 or directly to a conveyor belt situated further down.

The conveyor belt 44 drops the fresh material into a fresh-material bunker 46. Since the fresh material from four or more different bunkers is transported by one conveyor belt 44 and is heaped onto the same heap situated in the fresh-material bunker 46, the fresh material automatically undergoes a mixing process.

The fresh-material bunker 46 is an elongated chamber that connects the delivery and loading area 24 to the fermenter courtyard 18, as is shown in particular in FIG. 6. The fresh-material bunker 46 comprises a floor heater by means of which the fresh material is already preheated to a temperature of 42 DC in order to prevent the fermentation mass within a fermenter 16, 16', which fermentation mass is supplemented by the fresh material, from being cooled by said fresh material, so that after the fermenter 16 is closed the fermentation process starts up quickly, and possibly already a slightly aerobic prehydrolysis can take place that shortens the fermentation period and increases the output of the plant (throughput of fermentation substrate) and thus improves the efficiency of the plant.

The fresh-material bunker 46 assumes a dual function. Firstly, it is used as an interim storage area or a buffer storage area for loose fresh material. Secondly, it is used as a transport path between the delivery and loading area 24, in other words the periphery of the biomass power plant 10, and the centrally situated fermenter courtyard 18. For the purpose of conveyance a pusher blade or pusher (not shown) is arranged in the fresh-material bunker 46, which pusher blade or pusher pushes loose fresh material, which has been poured in anew from above, in the direction of the fermenter courtyard 18. After this the pusher is retracted in order to make room for new fresh material. By means of this pusher mechanism a situation is achieved in which the fresh material is pushed out of the fresh-material bunker 46, at the side of the fermenter courtyard 18, in approximately the same order in which it was placed into said fresh-material bunker 46. This means that the fresh material that reaches the fermenter courtyard 18 is always approximately of the same age and thus of a constant nature, which is advantageous in the subsequent fermentation process.

Furthermore, the delivery and loading area 24 comprises a section for the delivery and the transport of structured material or baled material, in particular of straw. This section for the delivery and the transport of baled material comprises a preparation space 48, a bale delivery space 50, a disintegration region 52 and an interim storage facility 54. Below, this region of the delivery and loading area 24 is described with reference to straw as a strongly lignified baled structural material, but it is understood that this section can also be used for the delivery, processing and onward transport of other baled structural material.

A crane (not shown) is affixed to a running rail in such a way that it can pick and place bales of straw in each of the spaces 48 to 54. The bales of straw are delivered to the straw delivery space 50 and are conveyed by the crane (not shown) to the interim storage facility 54. Before the straw is conveyed to the fermenter courtyard 18 it is pre-treated, namely disintegrated, in the disintegration region 52. Disintegration of the straw is necessary because the straw is strongly lignified, and as a result of the lignin-encrusted cellulose, the bacteria in the fermenter 16 find it very difficult to access the lignin-enclosed nutrients. Depending on the design of the biomass power plant 10, in the disintegration region 52 the straw can be disintegrated in various ways. For example, the straw can be chemically disintegrated in that it is soaked in a container comprising water, a water-lye solution or a water-acid solution. As a result of soaking, the lignin, which has largely enclosed the cellulose, is partly dissolved. After removal from the container the cellulose is no longer protected behind a lignin crust, but instead is accessible to hydrolysis and to bacteria. Consequently, straw, which in conventional wet- or dry-fermentation plants has hitherto only been used as a structure material, becomes a valuable fermentation substrate that makes a significant contribution to biogas development.

In an alternative embodiment, the straw in the disintegration region 52 can, however, also be disintegrated in some other way, for example mechanically with the use of a hammer mill, or by being subjected to thermal pressure, i.e. at high pressure of, for example, 20 to 30 bar, and being heated up for five to ten minutes to 180° C. to 250° C. In this process the lignin softens.

While the lignin solidifies again after the straw has cooled down, it does so in the form of very small spheres with interstitial spaces in-between, which spaces open the way for the autohydrolytic organic acids and for the anaerobic bacteria to gain access to the nutrients contained in the straw. A further exemplary embodiment relates to an expansion of the thermal pressure treatment, in which the pressure in the respective container is suddenly reduced, as a result of which the water in the straw structures flashes into steam and expands very rapidly. In this process the lignin structures are torn open, and the nutrients are rendered accessible to anaerobic bacteria. The remaining details relating to straw disintegration are stated in the following section.

In the preparation space 48 a roller conveyor 56 is provided, onto which individual bales of straw and/or packets of bales of straw are placed by the crane (not shown), wherein said roller conveyor 56 conveys the bales of straw, through a straw channel 58 that is arranged so as to be parallel to the fresh-material bunker 46, to the fermenter courtyard 18 (see FIG. 6).

As stated in the above description, both the loose fresh material and the baled fresh material are conveyed from the delivery and loading area 24 to the fermenter courtyard 18 by means of stationary materials handling technology. In this arrangement the fresh-material bunker 46 and the straw channel 58 establish the connection between the central fermenter courtyard 18 and the peripheral delivery and loading area 24, wherein this transport takes place entirely within the enclosed biomass power plant 10. Transport with stationary materials handling technology is suitable for large throughputs, and in particular is faster, more space-saving and more economical than delivery using wheel loaders. As shown in FIG. 6, the straw channel 58 and the fresh-material bunker 46 end at a central position in the fermenter courtyard 18 so that the paths between the fermenter-courtyard-end of the fresh-material bunker 46 or straw channel 58 and the fermenter 16 to be supplied are generally short.

As mentioned above, disintegration of the straw in the disintegration region 52 makes it possible to use straw as a fermentation substrate despite its high lignin content. This is extremely advantageous because straw arises anyway in the production of cereal crops, and because there is nowhere near adequate use for this straw. Since the biomass power plant 10 has been designed to use renewable resources, it is obvious that in the surroundings of the biomass power plant 10 resources be planted that are specifically suited for use in the biomass power plant 10, but which are usually not intended for foodstuffs. However, this presents a certain conflict of objectives, because a determined percentage of the limited available area is always reserved for the production of foodstuffs. The utilisation of straw as a fermentation substrate presents a very attractive solution, because straw, which arises anyhow in the production of cereal crops, at the same time allows the production of foodstuffs and of biomass that is suitable for use in power plants.

Straw offers yet another advantage. The fill height in fermenters is generally limited by the pressure that is present at the fermenter bottom. This pressure always needs to be sufficiently low for the fermentation substrate to still be permeable to percolate. However, if according to an embodiment of the invention a layer of bales of straw is placed in the lowermost position of each fermenter 16, the entire normal fill height of fermentation substance can still be stacked onto this layer, because the layer of bales of straw is still permeable to percolate even at the pressure that then occurs. The lowermost layer of straw thus represents an additional quantity of fermentation substrate, which quantity can be used in a fermenter, so that the plant output (volume output measured in new substrate per fermenter and day) is considerably improved.

In an advantageous embodiment of the invention, the bales of straw are placed on the roller conveyor 56 in packets comprising eight bales of straw, which packets comprise two bales in width and four bales in height. These packets are transported as a whole through the straw channel 58 and at its end, at the fermenter courtyard 18, are lifted off by a transfer device (not shown) and are passed over to a wheel loader or forklift truck, which also receives the packets as a whole or in two parts and conveys them to the fermenter. From these packets said lowermost layer of bales of straw can be built up relatively simply and quickly.

As is further shown in FIG. 8, a fermentation residues bunker 60 is provided that extends, parallel to the fresh-material bunker, between the fermenter courtyard 18 and the delivery and loading area 24. At its end facing the fermenter courtyard the fermentation residues bunker 60 comprises a feed bin 62 for fermentation residues, which feed bin 62 forms the entry to the fermentation residues bunker 60. A wheel loader tips fermentation residues into this feed bin 62. From there, said fermentation residues are pushed into the fermentation residues bunker by means of a screw-type conveyor. As a result of discontinuous pushing-in of a continuous flow of new fermentation residues the mass is slowly conveyed through the fermentation residues bunker 60 right up to its other end, where said fermentation residues are transported out of the fermentation residues bunker 60 by means of further screw-type conveyors.

The fermentation residues bunker 60 has a triple function. It not only provides a transport path between the fermenter courtyard 18 in the centre of the power plant 10 and the delivery and loading area, with similar advantages as they were described in the context of the fresh-material bunker 46 and the straw channel 58. The fermentation residues bunker 60 also serves as a thermophilically operated post-fermentation device, thus quasi acting as a further fermenter. This is the reason why the fermentation residues bunker 60 is connected to the biogas system.

Finally, the fermentation residues bunker 60 serves as an interim storage area for fermentation residues. It is dimensioned so that it holds at least the quantity of fermentation residues that can arise in a period of two days. This makes it possible to carry out outward transport of the arising fermentation residues on working days during the week only, without outward transport being restricted by any prohibition of truck traffic on weekends.

At the outlet end of the fermentation residues bunker 60 a distributing guide 64 is provided, which makes it possible to transport the fermentation residues either directly by way of a conveyor belt 66 to loading silos 68, or to make a detour by way of a dehydration device 70. In the exemplary embodiment shown, the dehydration device 70 is a screw-type press that is suitable for pressing water or percolate from the fermentation residues and feeding it into one of the percolate circulation tanks 34. A decision whether the detour by way of the dehydration device 70 is to take place depends on the actual demand for percolate.

The loading silos for fermentation residues 68 are tower silos that are arranged on trapezoidal frames so that a truck can drive underneath the silos 68 and can thus be easily loaded.

In an alternative embodiment a conventional drying plant, for example a drum-type or belt-type dryer (not shown), is provided that is suitable for drying the fermentation residues to a water content of below 25% preferably to 15%. In this arrangement the heat required for the drying plant is preferably provided by the waste heat from the generator sets. Furthermore, a gasification plant (not shown) is provided in which the dried fermentation residues are subjected to so-called wood gasification, in which combustible wood gas (weak gas) is produced from the dried fermentation residues by means of pyrolysis or partial combustion in a low-oxygen environment. Once the arising tar has been removed from the wood gas, this wood gas or weak gas is fed to the biogas system according to any known method, where it can then be used, completely unproblematically, as a fuel for the gas Otto engines.

The energy content of the wood gas reduces the requirement for biogas by up to 20%, and possibly more, so that in order to achieve an identical output of electrical current up to 20%, and possibly up to 30% less substrate needs to be used for fermentation. As a result of this the efficiency of the plant as a whole is considerably improved.

3. Disintegration of Straw

As mentioned in the introduction, in the biomass power plant shown, the straw is received in the delivery and loading area 24, and is disintegrated in the disintegration region 52 and possibly in addition in the preparation space 48. In this embodiment of the invention straw is delivered as a ligneous renewable resource in the form of bales and is also disintegrated in the form of bales before it is placed in the garage-type fermenter 16 in the form of bales. In this arrangement the density of bales preferably exceeds 200 kg/m3, a density that can only be achieved with very-high-pressure balers. Such high density of the bales of straw is associated with an advantage in that it makes optimal use of the capacity of a truck, both in relation to the permitted weight of the load and to the possible volume of the load, so that the straw can be delivered at economical conditions even over extended distances.

In the embodiment shown the pre-treatment for the disintegration of the straw involves four steps that are carried out in the disintegration region 52 or the preparation space 48, namely 1.) perforating the bales of straw,
2.) soaking the bales of straw in water,
3.) subjecting the soaked bales of straw to saturated-steam treatment, and
4.) soaking the bales of straw in percolate.

These steps and the devices used in their implementation are described below.

In a parallel stream, part of the straw can be used in the form of disintegration of "grinding" and/or in the form of disintegration of "thermal pressure hydrolysis". A combination of the various forms of disintegration is particularly advantageous because each one has its advantages and disadvantages in practical operation. A combination results in the best overall effect being achieved.

For example, irrespective of the pre-treatment of the remaining straw (or ligneous renewable resource in general), it is advantageous if part of the straw is ground, in particular to the consistency of powder, before it is added to the remaining fresh material. The ground straw results in a particularly high gas yield being achieved; however, the ratio to fresh material is limited to the extent that the pulverised straw that has been wetted by the percolate forms a sticky mass which for reasons of handling needs to be mixed with an adequate amount of fresh material.

Preferably, between 5 and 25 percent by weight of the fermentation substrate as a whole comprises ground straw. Preferably between 5% and 35% of the total quantity of straw is ground and thus mechanically disintegrated.

Furthermore, irrespective of the pre-treatment of the remaining straw (or ligneous renewable resource in general), it is advantageous if 5-20% of the total quantity of straw used is disintegrated by way of thermal pressure hydrolysis, and if the syrupy material obtained in this way, the so-called slurry, is placed into the circular flow of percolate.

Furthermore, irrespective of the remaining process steps, it is advantageous for the disintegration of straw to mechanically press-through the fermentation substrate that has been removed from the fermenter.

3.1. Perforation

Perforation of the bales of straw is used to make the interior of the bale of straw accessible to soaking, to saturated-steam treatment and to subsequent soaking in percolate. In the embodiment presently described, the bales of straw are perforated from two sides, as will be explained in more detail with reference to FIG. 10.

FIG. 10 at the top shows a perspective view of a bale 72 of straw, with a view onto its bottom 74. The lower diagram shows a perspective view of the same bale 72 of straw, with a view onto its top 76. From the bottom 74 the bale 72 of straw is perforated by a first set of holes 78, which do not extend through the entire bale 72. Furthermore, from the top 76 the bale 72 of straw is perforated by a second set of holes 80, which also do not extend through the entire bale 72 of straw. The holes 78 and 80 are offset relative to each other in such a way that the holes of the first set 78 and the holes of the second set 80 are separated from each other by material bridges. As a result of this type of perforation, the soaking water of the second step, the saturated steam of the third step and the percolate of the fourth step are able to penetrate into the interior of the bale 72 of straw without dripping out on the other side.

3.2. Soaking

In the disintegration space 52 of FIG. 8 suitable containers for soaking bales of straw are provided, which are not shown in the illustration. The size of the containers for soaking is tailored to the dimensions of the bales of straw so that soaking can be carried out in a space-saving and efficient manner.

3.3. Saturated-Steam Treatment

In the disintegration region 52 or in the preparation space 48 a device for saturated-steam treatment is provided. With reference to FIGS. 11 to 14 various devices for saturated-steam treatment are described, which devices can be used in the plant shown or in a modified plant.

FIG. 11 shows a diagrammatic cross-sectional view of a simple design of a device 82 for saturated-steam treatment. The device 82 comprises a pressure vessel 84 with a lid 83 that is hinged to the pressure vessel 84 by way of a joint 85. A feed device for the straw is diagrammatically shown and designated by reference character 87. If the device 82 for saturated-steam treatment is to be used for the treatment of bales of straw, the feed device 87 can, for example, comprise a conveyor belt or a roller conveyor. If the device 82 is to be used for loose ligneous renewable resources, for example for loose straw 106, the feed device 87 can comprise rails along which a container 89 for loose material can be pushed into the pressure vessel 84. The container 89 is permeable to steam, but is suitable for holding the loose material; it can, for example, be an open-top mesh container or basket. The lid 83 of the pressure vessel 84 can be closed by means of a closing mechanism 91. Preferably, in order to open the pressure vessel 84 the lid 83 is hinged inwards as shown, for example, in FIG. 14 so that as a result of the pressure in the interior of the pressure vessel 84 the lid 83 is pushed into its closed position and in this manner is sealed more easily.

The pressure vessel 84 is connected to an infeed pipe 93 and a feed valve 95 through which saturated steam 102 at a pressure of up to 30 bar and a temperature of up to 250° C. can be fed from a steam reservoir (not shown) to the pressure vessel 84. Furthermore, the pressure vessel 84 is connected to an outlet pipe 97 comprising an outlet valve 98 by way of which the steam can be let out of the pressure vessel 84 after saturated-steam treatment. Furthermore, in the outlet pipe 97 a compressor 100 is arranged, by means of which compressor 100 saturated steam 102 can be conveyed back into the reservoir (not shown).

Below, the process of saturated-steam treatment is explained with reference to the device 82 for saturated-steam treatment of FIG. 11. First the ligneous material 106 is placed as a bale or as loose material into a container, for example like container 89, in the pressure vessel 84, and then said pressure vessel 84 is closed. Thereafter the valve 95 in the infeed pipe 93 is opened so hot steam at a temperature of 180° C. to 250° C. and at high pressure of between 20 and 30 bar is introduced from a steam reservoir (not shown) into the pressure vessel 84. The introduced saturated steam is diagrammatically indicated in FIG. 11 and is designated by reference character 102.

The ligneous material 106 is exposed to the saturated steam 102 for 5 to 15 minutes. In this process the lignin in the material is melted but is not dissolved out of the material. It is advantageous for the efficiency of saturated-steam treatment if the material, e.g. the straw, was previously soaked in the above-mentioned second step, because the water is then already present in the material and only needs to be heated therein, which shortens the duration of treatment.

After a predetermined dwell time of 5 to 15 minutes the saturated steam is let out of the pressure vessel 84 by way of the outlet pipe 97. Preferably, this pressure release takes place instantaneously so that the pressure is reduced by at least 80% within 5 seconds or less. As a result of the rapid drop in pressure the water in the structures of the ligneous material flashes instantly into steam, and in this process expands rapidly. In this process the ligneous structures of the straw are torn open so that the nutrients (cellulose and arabinoxylane) become accessible to aqueous organic acids and to anaerobic bacteria.

After the pressure has been released from the pressure vessel 84, the ligneous material 106 is removed from the pressure vessel 84 and cools down. During cooling, the melted lignin returns to its solidified state. However, during solidification of the lignin there is no reversion to the original sheet-like structures; instead the lignin coagulates to form a droplet structure which leaves interstitial spaces through which at first organic acids and then bacteria can gain access to the cellulose and to the arabinoxylane (hemi-cellulose).

The basic design, shown in FIG. 11 of the device 82 for saturated-steam treatment can be modified in a host of ways, with a few example of such modifications being provided below. In the description, identical or functionally equivalent components have the same reference characters as in FIG. 11, wherein their description is not repeated.

FIG. 12 shows a design of a device for saturated-steam treatment, which device is intended for quasi continuous processing of loose material. Here again, in the interior of the pressure vessel 84 a container 89 for loose material 106 is provided, except that said container 89 has been installed so as to be affixed in the pressure vessel 84. In order to fill the container 89 a pressure-resistant slide 108 is opened so that the ligneous material 106 falls from a funnel 110 into the container 88. When an adequate quantity of material 106 is in the container 89, the pressure-resistant slide 108 is closed, and saturated-steam treatment takes place in the same manner as described with reference to FIG. 11. In addition to the components of FIG. 11, however, FIG. 12 also shows a reservoir 112 for saturated steam 102, which reservoir 112 comprises a heater 114. After the saturated-steam treatment the steam is released by way of the outlet pipe 97, and is pushed into the reservoir 112 by way of the compressor 100. After this, a further pressure-resistant slide 108 at the bottom end of the container is opened, and the disintegrated loose material 106 falls onto a conveyor belt 116 for onward transport.

At the lower end of the container 84, in particular during thermal pressure hydrolysis, a slurry 117 collects, which is let off by way of a further pipe 118 and is fed into the percolate circulation tanks (not shown) by way of a pipe 120.

FIG. 13 shows a further embodiment 122 of a device for saturated-steam treatment, which is specifically designed for the treatment of baled material, in particular bales 72 of straw. Its design is basically similar to the design of FIG. 11 and is therefore not described anew. However, there is a significant difference in that a lance or spike 124 is provided which comprises an interior hollow space 126 and nozzle-like openings 128 connected to this interior hollow space 126. The interior hollow space 126 is in fluid connection with the infeed pipe 93.

During operation of the device for saturated-steam treatment 122 of FIG. 13, a bale 72 of straw or 106 is placed, by way of the feed device 87, which in the embodiment shown is formed by a roller path, in the illustration of FIG. 13 from the right-hand side, into the pressure vessel 84, and is speared onto the lance 124. After this the pressure vessel 84 is closed, as already explained, and the saturated steam 102 is injected into the bale 72 of straw by way of the infeed pipe 93, the interior hollow space 126 of the lance 124 and the nozzle-like openings 128. In this way it is ensured that the interior of the bale 72 of straw also effectively comes into contact with the saturated steam. Because, if the saturated steam is merely fed to the material from the outside, as shown in FIG. 11, it can happen, in particular in the case of a highly compressed bale 72, that the saturated steam does not establish adequate contact with the material in the interior of the bale. Instead, the air contained in the bale is compressed, by the highly pressurised steam, in the interior of the bale, possibly without adequately mixing with the hot steam during the relatively short treatment times. The use of the lance 124 ensures thorough saturated-steam treatment also in the interior of the bale 72.

Finally, FIG. 14 shows a further device 130 for saturated-steam treatment, which device 130 comprises five pressure vessels 84 that comprise lances 124 in a manner similar to that of the device 122 of FIG. 13. However, in the device 130 of FIG. 14 the pressure vessels 84 are arranged vertically so that the bales of straw can be placed into the pressure vessels 84 from the top by means of a crane 132. The crane 132 comprises a crane trolley 134 and a frame 136 that comprises a top pick-up device 138 for a top bale, and a bottom pick-up device 140 for a bottom bale. By means of the crane 130 is thus possible to pick up two bales 72 of straw that are arranged vertically one on top of the other, to place them from the top into the pressure vessel 84, and to spear them onto a lance 124 that for this purpose is approximately twice as long as the lance 124 of FIG. 13.

All the pressure vessels 84 of FIG. 14 are connected to the same pressure reservoir 112 by way of a pipeline. In this arrangement in a manner similar to that of FIG. 13, the saturated steam 102 is in each case introduced into the pressure vessel 84 through the feed pipe 92, through the lance 124 and through the bales 72 of straw.

The improvement of FIG. 14 is designed for a high-throughput plant in which saturated-steam treatment can be carried out very efficiently.

3.4 Soaking in Percolate or Similar

In the fourth process step mentioned above the pre-treated bales are soaked in percolate that represents a slightly acid solution. As an alternative, the bales can, however, also be soaked in a slightly alkaline solution, for example a caustic lye of soda. After the soaking process, the bales are heated to approximately 40 DC, which can, for example, be achieved in that the straw channel 46 (see FIG. 8) is heated by the exhaust heat of the gas Otto engines. By soaking the material after saturated-steam treatment and before anaerobic bacterial fermentation, a slightly aerobic prehydrolysis is initiated through which the subsequent anaerobic bacterial fermentation is accelerated once again. During soaking in percolate the anaerobic bacteria are already in the location of fresh material which is also advantageous.

It is important to note that with the presently described process for the disintegration of a ligneous renewable resource, in particular of straw, the pre-treated material in the fermenters returns a significant gas yield with moderate dwell times, and, moreover, this is achieved without the addition of enzymes, fungi or yeasts. Even without such addition, the existing natural acid content of the straw (approximately 3 to 4%) dissolves the solid cellulose and transforms it to an aqueous solution (autohydrolysis). As a result of the action of the organic acid and/or as a result of the influence of bacteria, the biogenic polymers are chemically and/or biochemically decomposed to form low-molecular weight compounds (monosaccharides, amino acids, short-chain peptides, long-chain fatty acids, glycerine). At the end of the phase they are present in water-dissolved form. However, this takes place without first having to add enzymes, bacteria or yeasts. In this embodiment the ligneous material is solely left to autohydrolysis and to bacterial hydrolysis.

The disintegration which has been described in detail in this document, which disintegration comprises the four process steps stated above, is extremely effective and advantageous, but it is not mandatory for all four steps to be used; instead, simpler processes with fewer steps, or with only a selection of the steps, can be carried out that still support fermentation of ligneous renewable resources. In particular, useful disintegration of the ligneous material can be achieved if prior to being placed into the fermenter, said ligneous material is only mixed with solid manure and/or liquid manure, because the urea contained therein can already soften the lignin structures. In this arrangement it is not even mandatory for the ligneous renewable resource to be mixed with liquid manure or solid manure before being placed in the fermenter; instead, it may already be sufficient for the ligneous renewable resources and solid manure to be layered in alternate layers in the fermenter, if applicable with intermediate layers of other, non-lignified, renewable resources, wherein the urea of the upper layers of solid manure together with the percolate enters the layer comprising the ligneous material, and in this way at least partly dissolves the sheet-like lignin structures. This represents a very simple case of chemical disintegration.

Although the drawings and the above description shows and describes in detail a preferred exemplary embodiment of the invention, this should be interpreted as purely exemplary and not limiting the invention. It should be pointed out that only the preferred exemplary embodiment is shown and described, and any and all changes and modifications that are presently, and that will in future be, within the scope of protection of the invention are to be protected.

LIST OF REFERENCE CHARACTERS

10 Biomass power plant
12 Base section
14 Expansion section
16 Fermenter
18 Fermenter courtyard
20 Fermenter door
22 Power and heat generating plant
24 Delivery and loading area
26 Hall section of the fermenter courtyard
28 Hall section of the delivery and loading area
30 Engineered bridge
31 Waste-gas cooling space
32 Foil gas-storage device
34 Percolate circulation tank
36 Southern room comprising technical equipment
38 Northern room comprising technical equipment
40 Illumination strips
42 Delivery bunker for fresh material
44 Conveyor belt
46 Fresh-material bunker
48 Preparation space
50 Bale delivery space
52 Disintegration region
54 Interim storage facility
56 Roller conveyor
58 Straw channel
60 Fermentation residues bunker
62 Feed bin for fermentation residues
65 Distributing guide for fermentation residues
66 Conveyor belt for fermentation residues
68 Loading silos for fermentation residues
70 Dehydration device
72 Bale of straw
74 Bottom of the bale 72 of straw
76 Top of the bale 72 of straw
78 First set of holes
80 Second set of holes
82 Device for saturated-steam treatment
83 Lid
84 Pressure vessel
85 Hinge
86 Central gas-distribution storage device
87 Feed device
88 Motor installation space
89 Container
90 Device for incoming air to motor installation spaces
91 Closing mechanism
92 Device for outgoing air from motor installation spaces
93 Infeed pipe
94 Docking station
95 Feed valve
96 Storage facility
97 Outlet pipe
98 Outlet valve
100 Compressor
102 Saturated steam
103 Issuing saturated steam
104 Device for saturated-steam treatment
106 Ligneous renewable resource
108 Pressure-resistant slide
110 Funnel
112 Steam reservoir
114 Heater
116 Conveyor belt
117 Slurry
118 Pipe connection
120 Pipe to the percolate circulation tank
122 Device for saturated-steam treatment
124 Lance
126 Interior hollow space
128 Opening in the lance 124
130 Device for saturated-steam treatment
132 Crane
134 Crane trolley
136 Frame
138 Pick-up device for top bale
140 Pick-up device for bottom bale

The invention claimed is:

1. A biogas plant for the production of biogas, comprising: a plurality of garage-type fermenters configured to carry out anaerobic bacterial fermentation of biomass via a solid-state fermentation process, a device configured to mill ligneous renewable resources, wherein the ligneous renewable resources comprise straw; a device configured to thermally disintegrate ligneous renewable resources, and wherein the device configured to thermally disintegrate ligneous renewable resources comprises a device configured to carry out a saturated-steam treatment.

2. The biogas plant according to claim 1, wherein the device configured to carry out the saturated-steam treatment comprises a pressure vessel and means that are suitable for generating steam in the pressure vessel at a pressure of between 20 and 30 bar, and at a temperature of between 180° C. and 250° C.

3. The biogas plant according to claim 1, wherein the device configured to carry out the saturated-steam treatment comprises at least one lance onto which a bale containing ligneous renewable resources can be speared, wherein the at least one lance comprises an interior hollow space into which steam can be introduced, and comprises a plurality of openings through which the steam can issue from the hollow space.

4. The biogas plant according to claim 1, wherein in a pressure vessel a container that is permeable to steam is provided, wherein the container is configured to retain loose ligneous renewable resources.

5. The biogas plant according to claim 4, further comprising means for transporting the container that is permeable to steam into and out of the pressure vessel.

6. The biogas plant according to claim 4, wherein the container that is permeable to steam comprises a top opening configured to receive loose ligneous renewable resources, and a bottom opening configured to allow the loose ligneous renewable resources to fall out of the container that is permeable to steam.

7. The biogas plant according to claim 1, wherein the device configured to carry out the saturated-steam treatment comprises several pressure vessels that are interconnected via pipelines.

8. The biogas plant according to claim 1, further comprising a perforator configured to perforate bales of a ligneous renewable resource.

9. The biogas plant according to claim 8, wherein the perforator is configured to perforate a bale from two sides in such a manner that holes resulting from perforation from one side, and holes resulting from perforation from an other side are separated by bridges of material.

10. The biogas plant according to claim 1, further comprising a device configured to chemically disintegrate ligneous renewable resources comprising a an additional container for soaking said ligneous renewable resources in water, a water-lye solution, a water-acid solution, percolate or liquid manure.

11. The biogas plant according to claim 1, wherein at least one of the device configured to mill ligneous renewable resources and the device configured to thermally disintegrate ligneous renewable resources is accommodated in a delivery and loading area.

12. The biogas plant according to claim 11, wherein the delivery and loading area comprises stationary materials handling technology configured to convey fresh material from the delivery and loading area to a fermenter courtyard from which the plurality of garage-type fermenters are accessible.

13. The biogas plant according to claim 11, wherein the delivery and loading area comprises at least one enclosed delivery bunker for fresh material.

14. The biogas plant according to claim 13, further comprising first conveyor means that are suitable for conveying fresh material from the at least one enclosed delivery bunker for fresh material to a fresh-material bunker.

15. The biogas plant according to claim 14, wherein the first conveyor means comprises a conveyor belt on which the fresh material is conveyable from various delivery bunkers to the fresh-material bunker.

16. The biogas plant according to claim 14, further comprising second conveyor means suitable for conveying the fresh material through the fresh-material bunker in the direction of the fermenter courtyard.

17. The biogas plant according to claim 11, further comprising an unloading point for baled material.

18. The biogas plant according to claim 17, wherein at the unloading point for baled material a crane is provided that is configured to pick or grip and convey the baled material.

19. The biogas plant according to claim 17, further comprising third conveyor means suitable for conveying individual bales or packets of bales along a bale channel to the fermenter courtyard.

20. The biogas plant according to claim 17, further comprising a transfer device that is arranged on that end of a bale channel that faces the fermenter courtyard, wherein the transfer device is configured to remove packets of bales from the bale channel and pass them over as a packet to a wheel loader or forklift truck.

21. The biogas plant according to claim 13, wherein the at least one enclosed delivery bunker, the fresh-material bunker, a bale channel or a combination thereof is heatable.

22. The biogas plant according to claim 21, wherein the at least one enclosed delivery bunker, the fresh-material bunker, the bale channel or a combination thereof is heatable via waste heat that is generated by one or several gas engines.

23. The biogas plant according to claim 1, further comprising a fermentation residues bunker that for the placement of fermentation residues is accessible from the fermenter courtyard.

24. The biogas plant according to claim 23, wherein the fermentation residues bunker comprises stationary conveyor means that are suitable for transporting fermentation residues away through the fermentation residues bunker.

25. The biogas plant according to claim 24, wherein the stationary conveyor means comprise screw conveyors that are arranged on the ends of the fermentation residues bunker.

26. The biogas plant according to claim 23, wherein the fermentation residues bunker is dimensioned so that it holds the expected quantity of fermentation residues that arises over at least two days.

27. The biogas plant according to claim 23, wherein the fermentation residues bunker is connected to the biogas system.

28. The biogas plant according to claim 23, further comprising a feed bin configured to feed the fermentation residues, wherein the feed bin is arranged at an inlet end of the fermentation residues bunker.

29. The biogas plant according to claim 23, further comprising a device configured to dehydrate the fermentation residues, wherein the device configured to dehydrate the fermentation residues is provided at an outlet end of the fermentation residues bunker.

30. The biogas plant according to claim 1, further comprising a gasification plant configured to generate wood gas or weak gas from dried fermentation residues via a method of wood gasification.

31. The biogas plant according to claim 1, further comprising a drying plant configured to dry fermentation residues.

32. The biogas plant according to claim 17, wherein the baled material is straw.

33. The biogas plant according to claim 1, wherein the device configured to mill ligneous renewable resources comprises a hammer mill.

34. The biogas plant according to claim 1, wherein the biogas plant produces methane.

35. The biogas plant according to claim 16, wherein the second conveyor means comprises a pusher blade.

36. The biogas plant according to claim 19, wherein the third conveyor means comprise roller conveyors or push conveyors.

37. A process for the production of biogas from ligneous renewable resources using the biogas plant of claim 1, comprising the following steps:
pre-treating a ligneous renewable resource in order to effect chemical, thermal and/or mechanical disintegration thereof, placing the pre-treated ligneous renewable resource into a garage-type fermenter, and creating conditions in the garage-type fermenter that support anaerobic bacterial fermentation according to a solid-state fermentation process.

38. The process according to claim 37, wherein the saturated-steam treatment is carried out in such a manner that it softens the lignin structures of the ligneous renewable resource, while on the whole the exterior structure of the resource overall essentially remains intact.

39. The process according to claim 37, wherein the saturated-steam treatment is carried out at a temperature of between 160° C. and 240° C. and a pressure of between 20 and 30 bar for less than 20 minutes.

40. The process according to claim 37, wherein the treatment pressure at the end of the saturated-steam treatment is reduced by at least 80% within five seconds.

41. The process according to claim 37, wherein the ligneous renewable resource is soaked before saturated-steam treatment takes place.

42. The process according to claim 37, wherein after saturated-steam treatment the ligneous renewable resource is soaked in an acid solution, in an alkaline solution or in liquid manure.

43. The process according to claim 37, wherein the ligneous renewable resource is subjected to mechanical size-reduction before saturated-steam treatment takes place.

44. The process according to claim 37, wherein the ligneous renewable resource is provided in the form of bales.

45. The process according to claim 31, wherein the ligneous renewable resource is straw, and the bales comprise a density of at least 200 kg/m$^3$.

46. The process according to claim 31, wherein the bales are perforated from at least one side.

47. The process according to claim 33, wherein the holes do not extend all the way through the bale.

48. The process according to claim 33, wherein the bale is perforated from two opposite sides, wherein the position of the holes is selected so that the holes of the one side and the holes of the other side are separated by material bridges.

49. The process according to claim 44, wherein for saturated-steam treatment the bales are speared onto at least one lance, and the steam is introduced into the interior of the bale through openings in the at least one lance.

50. The process according to claim 44, wherein the bales are placed as the lowermost layer into a fermenter.

51. The process according to claim 37, wherein chemical pre-treatment involves mixing the ligneous renewable resource with solid manure, liquid manure, percolate and/or percolate-containing fermentation mass.

52. The process according to claim 37, wherein chemical pre-treatment involves soaking the ligneous renewable resource in a water-acid solution, a water-lye solution, percolate or liquid manure.

53. The process according to claim 37, wherein pre-treatment of the ligneous renewable resource for mechanical disintegration involves shredding or grinding said resource.

54. The process according to claim 37, wherein between pre-treatment and anaerobic fermentation no acids, enzymes, fungi or yeasts are fed to the ligneous renewable resource.

55. The process according to claim 37, wherein fermentation residues are dried to a water content of below 25%, and are gasified to produce wood gas or weak gas.

56. The process according to claim 42, wherein after saturated-steam treatment the ligneous renewable resource is soaked in the acid solution, and the acid solution comprises percolate.

57. The process according to claim 44, wherein the ligneous renewable resource is straw, and the bales comprise a density of at least 208 kg/m$^3$.

58. The process according to claim 37, wherein fermentation residues are dried to a water content of below 15%, and are gasified to produce wood gas or weak gas.

* * * * *